(12) United States Patent
Wells et al.

(10) Patent No.: US 9,329,169 B2
(45) Date of Patent: May 3, 2016

(54) VIVO ISOTOPIC LABELING METHOD FOR QUANTITATIVE GLYCOMICS

(75) Inventors: Robert Lance Wells, Athens, GA (US); Ronald C. Orlando, Athens, GA (US); Stephen Dalton, Athens, GA (US); Kelley W. Moremen, Bishop, GA (US); James Michael Pierce, Athens, GA (US); James A. Atwood, III, Washington, GA (US); Michael Tiemeyer, Watkinsville, GA (US); William S. York, Watkinsville, GA (US)

(73) Assignee: UNIVERSITY OF GEORGIA RESEARCH FOUNDATION, INC, Athens, GA (US)

( * ) Notice: Subject to any disclaimer, the term of this patent is extended or adjusted under 35 U.S.C. 154(b) by 1356 days.

(21) Appl. No.: 12/734,102

(22) PCT Filed: Oct. 29, 2008

(86) PCT No.: PCT/US2008/012283
§ 371 (c)(1),
(2), (4) Date: Jul. 30, 2010

(87) PCT Pub. No.: WO2009/058307
PCT Pub. Date: May 7, 2009

(65) Prior Publication Data
US 2010/0297609 A1 Nov. 25, 2010

Related U.S. Application Data

(60) Provisional application No. 61/000,920, filed on Oct. 29, 2007.

(51) Int. Cl.
*C12Q 1/02* (2006.01)
*G01N 33/50* (2006.01)
*G01N 33/68* (2006.01)

(52) U.S. Cl.
CPC .......... *G01N 33/502* (2013.01); *G01N 33/6848* (2013.01); *G01N 2400/00* (2013.01); *G01N 2400/12* (2013.01); *G01N 2400/38* (2013.01); *G01N 2458/15* (2013.01)

(58) Field of Classification Search
CPC .......... G01N 2458/15; G01N 2400/38; G01N 2400/00; G01N 33/502; G01N 2400/12; G01N 33/6848
USPC ...................................................... 435/5, 29
See application file for complete search history.

(56) References Cited

U.S. PATENT DOCUMENTS 6,391,649 B1 5/2002 Chait et al.
6,642,059 B2 11/2003 Chait et al.
6,653,076 B1 11/2003 Franza, Jr. et al.
2008/0113441 A1 5/2008 Orlando et al.
2009/0104603 A1* 4/2009 Satomaa et al. .................. 435/6

FOREIGN PATENT DOCUMENTS

WO WO 99/53021 * 10/1999

OTHER PUBLICATIONS

Street et al. (A 1H/15N n.m.r. study of nitrogen metabolism in cultured mammalian cells, 1993, Biochem. J., vol. 291, pp. 485-492).*
Kratchmarova et al. (Mechanism of divergent growth factor effects in mesenchymal stem cell differentiation, 2005, Science, vol. 308, pp. 1472-1477 and supplemental materials, 13 pages, 20 pages total).*
Kornfeld (Studies on I-glutamine d-fructose 6-phosphate amidotransferase, 1967, The Journal of Biological Chemistry, vol. 242, pp. 3135-3141).*
Adler (Glutamine fructose-6-phosphate aminotransferase and glycoprotein synthesis in the developing chick eye, 1984, Current Eye Research, vol. 3, pp. 351-362).*
Liu, H.; Sadygov, R. G.; Yates, J. R., 3rd, A model for random sampling and estimation of relative protein abundance in shotgun proteomics. Anal Chem 2004, 76, (14), 4193-201.
Radulovic, D.; Jelveh, S.; Ryu, S.; Hamilton, T. G.; Foss, E.; Mao, Y.; Emili, A., Informatics platform for global proteomic profiling and biomarker discovery using liquid chromatography-tandem mass spectrometry. Mol Cell Proteomics 2004, 3, (10), 984-97.
Silva, J. C.; Denny, R.; Dorschel, C. A.; Gorenstein, M.; Kass, I. J.; Li, G. Z.; McKenna, T.; Nold, M. J.; Richardson, K.; Young, P.; Geromanos, S., Quantitative proteomic analysis by accurate mass retention time pairs. Anal Chem 2005, 77, (7), 2187-200.
Wang, W.; Zhou, H.; Lin, H.; Roy, S.; Shaler, T. A.; Hill, L. R.; Norton, S.; Kumar, P.; Anderle, M.; Becker, C. H., Quantification of proteins and metabolites by mass spectrometry without isotopic labeling or spiked standards. Anal Chem 2003, 75, (18), 4818-26.
Gygi, S. P.; Rist, B.; Gerber, S. A.; Turecek, F.; Gelb, M. H.; Aebersold, R., Quantitative analysis of complex protein mixtures using isotope-coded affinity tags. Nat Biotechnol 1999, 17, (10), 994-9.
Liu, P.; Regnier, F. E., An isotope coding strategy for proteomics involving both amine and carboxyl group labeling. J Proteome Res 2002, 1, (5), 443-50.
Ong, S. E.; Blagoev, B.; Kratchmarova, I.; Kristensen, D. B.; Steen, H.; Pandey, A.; Mann, M., Stable isotope labeling by amino acids in cell culture, SILAC, as a simple and accurate approach to expression proteomics. Mol Cell Proteomics 2002, 1, (5), 376-86.
Rao, K. C.; Carruth, R. T.; Miyagi, M., Proteolytic 18O labeling by peptidyl-Lys metalloendopeptidase for comparative proteomics. J Proteome Res 2005, 4, (2), 507-14.

(Continued)

*Primary Examiner* — Sharmila G. Landau
*Assistant Examiner* — Shannon Janssen
(74) *Attorney, Agent, or Firm* — Henry D. Coleman; R. Neil Sudol

(57) ABSTRACT

The present invention relates to a method of isotopically labeling glycans and in facilitating high throughput quantitative/comparative analysis of glycomic compositions of biological cells. The method is applicable inter alia for identifying differentiated cells and their glycomic characteristics, differentiation conditions, disease and/or therapeutic progression, diagnosing disease states, determining drug activity, establishing manufacturing efficiencies and for determining the half-life of glycans in cells.

20 Claims, 16 Drawing Sheets

(56) References Cited

OTHER PUBLICATIONS

Schnolzer, M.; Jedrzejewski, P.; Lehmann, W. D., Protease-catalyzed incorporation of 18O into peptide fragments and its application for protein sequencing by electrospray and matrix-assisted laser desorption/ionization mass spectrometry. Electrophoresis 1996, 17, (5), 945-53.

Vosseller, K.; Hansen, K. C.; Chalkley, R. J.; Trinidad, J. C.; Wells, L.; Hart, G. W.; Burlingame, A. L., Quantitative analysis of both protein expression and serine / threonine post-translational modifications through stable isotope labeling with dithiothreitol. Proteomics 2005, 5, (2), 388-98.

Wells, L.; Vosseller, K.; Cole, R. N.; Cronshaw, J. M.; Matunis, M. J.; Hart, G. W., Mapping sites of O-GlcNAc modification using affinity tags for serine and threonine post-translational modifications. Mol Cell Proteomics 2002, 1, (10), 791-804.

Yao, X.; Freas, A.; Ramirez, J.; Demirev, P. A.; Fenselau, C., Proteolytic 18O labeling for comparative proteomics: model studies with two serotypes of adenovirus. Anal Chem 2001, 73, (13), 2836-42.

Ong, S. E.; Foster, L. J.; Mann, M., Mass spectrometric-based approaches in quantitative proteomics. Methods 2003, 29, (2), 124-30.

Aoki, K.; Perlman, M.; Lim, J. M.; Cantu, R.; Wells, L.; Tiemeyer, M., Dynamic developmental elaboration of N-linked glycan complexity in the *Drosophila melanogaster* embryo. J Biol Chem 2007, 282, (12), 9127-42.

Bowman, M. J.; Zaia, J., Tags for the stable isotopic labeling of carbohydrates and quantitative analysis by mass spectrometry. Anal Chem 2007, 79, (15), 5777-84.

Hitchcock, A. M.; Costello, C. E.; Zaia, J., Glycoform quantification of chondroitin/dermatan sulfate using a liquid chromatography-tandem mass spectrometry platform. Biochemistry 2006, 45, (7), 2350-61.

Xia, B.; Kawar, Z. S.; Ju, T.; Alvarez, R. A.; Sachdev, G. P.; Cummings, R. D., Versatile fluorescent derivatization of glycans for glycomic analysis. Nat Methods 2005, 2, (11), 845-50.

Yuan, J.; Hashii, N.; Kawasaki, N.; Itoh, S.; Kawanishi, T.; Hayakawa, T., Isotope tag method for quantitative analysis of carbohydrates by liquid chromatography-mass spectrometry. J Chromatogr A 2005, 1067, (1-2), 145-52.

Xie, Y.; Liu, J.; Zhang, J.; Hedrick, J. L.; Lebrilla, C. B., Method for the comparative glycomic analyses of O-linked, oligosaccharides. Anal Chem 2004, 76, (17), 5186-97.

Alvarez-Manilla, G.; Warren, N. L.; Abney, T.; Atwood, J., 3rd; Azadi, P.; York, W. S.; Pierce, M.; Orlando, R., Tools for glycomics: relative quantitation of glycans by isotopic permethylation using 13CH3I. Glycobiology 2007, 17, (7), 677-87.

Kang, P.; Mechref, Y.; Kyselova, Z.; Goetz, J. A.; Novotny, M. V., Comparative glycomic mapping through quantitative permethylation and stable-isotope labeling. Anal Chem 2007, 79, (16), 6064-73.

Atwood, J. A., 3rd; Cheng, L.; Alvarez-Manilla, G.; Warren, N. L.; York, W. S.; Orlando, R., Quantitation by isobaric labeling: applications to glycomics. J Proteome Res 2008, 7, (1), 367-74.

Bothelo, J. C.; Atwood, J. A., 3rd; Cheng, L.; Alvarez-Manilla, G.; York, W. S.; Orlando, R., QUIBL for the Comparative Glycomic Study of O-linked Glycans. International Journal of Mass Spectrometry 2008, 278, 137-142.

Stead, E.; White, J.; Faast, R.; Conn, S.; Goldstone, S.; Rathjen, J.; Dhingra, U.; Rathjen, P.; Walker, D.; Dalton, S., Pluripotent cell division cycles are driven by ectopic Cdk2, cyclin A/E and E2F activities. Oncogene 2002, 21, (54), 8320-33.

Aoki, K.; Porterfield, M.; Lee, S. S.; Dong, B.; Nguyen, K.; McGlamry, K. H.; Tiemeyer, M., The diversity of O-linked glycans expressed during *Drosophila melanogaster* development reflects stage- and tissue-specific requirements for cell signaling. J Biol Chem 2008, 283, (44), 30385-30400.

McClain, D. A., Hexosamines as mediators of nutrient sensing and regulation in diabetes. J Diabetes Complications 2002, 16, (1), 72-80.

Yki-Jarvinen, H.; Vogt, C.; Iozzo, P.; Pipek, R.; Daniels, M. C.; Virkamaki, A.; Makimattila, S.; Mandarino, L.; DeFronzo, R. A.; McClain, D.; Gottschalk, W. K., UDP-N-acetylglucosamine transferase and glutamine: fructose 6-phosphate amidotransferase activities in insulin-sensitive tissues. Diabetologia 1997, 40, (1), 76-81.

Kean, E. L.; Munster-Kuhnel, A. K.; Gerardy-Schahn, R., CMP-sialic acid synthetase of the nucleus. Biochim Biophys Acta 2004, 1673, (1-2), 56-65.

Thoden, J. B.; Wohlers, T. M.; Fridovich-Keil, J. L.; Holden, H. M., Human UDP-galactose 4-epimerase. Accommodation of UDP-N-acetylglucosamine within the active site. J Biol Chem 2001, 276, (18), 15131-6.

Wells, L.; Vosseller, K.; Hart, G. W., Glycosylation of nudeocytoplasmic proteins: signal transduction and O-GlcNAc. Science 2001, 291, (5512), 2376-8.

G. Alvarez-Manilla, et al., "Tools for glycomics: relative quantitation of glycans by isotopic permethylation using 13CH31" Glycobiology vol. 17(7):677-687, Mar. 23, 2007 online publication.

M.J. Bowman and J. Zaia, "Novel Tags for the stable isotopic labeling of carbohydrates and quantitative analysis by mass spectrometry" Anal. Chem. vol. 79(15):5777-5784 (Aug. 1, 2007).

A. Kameyama, et al., Strategy for simulation of CID spectra of N-linked oligosaccharides towards glycomics: J. Proteome Res. vol. 5(4):808-814, Mar. 21, 2006 online publication.

A.M. Hitchicock, et al., Glycoform quantification of chondroitin/dermatan sulfate using a liquid chromatography-tandem mas spectrometry platform: Biochemistry vol. 45(7):2350-2361, Jan. 31, 2006 online publication.

\* cited by examiner

Figure 2 (cont.)

| No. | Structure | No. of N | z | [M+xNa]^x+ (mono) Amide-14N-Gln | [M+xNa]^x+ (mono) Amide-15N-GLN | ΔM (m/z) |
|---|---|---|---|---|---|---|
| 1 | 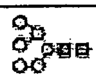 | 2 | 2 | 903.436 | 904.433 | 0.997 |
| 2 | 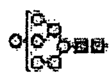 | 2 | 2 | 1005.486 | 1006.483 | 0.997 |
| 3 | 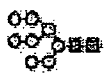 | 2 | 2 | 1107.536 | 1108.533 | 0.997 |
| 4 | 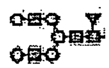 | 4 | 2 | 1133.557 | 1135.551 | 1.994 |
| 5 | 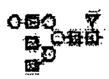 | 5 | 2 | 1154.071 | 1156.563 | 2.493 |
| 6 | 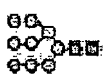 | 2 | 2 | 1209.586 | 1210.583 | 0.997 |
| 7 | 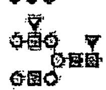 | 4 | 2 | 1220.602 | 1222.596 | 1.994 |
| 8 | 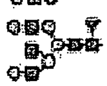 | 5 | 2 | 1256.121 | 1258.613 | 2.493 |
| 9 | 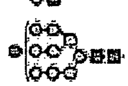 | 2 | 2 | 1311.636 | 1312.633 | 0.997 |
| 10 | 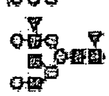 | 5 | 2 | 1343.165 | 1345.658 | 2.493 |
| 11 | 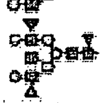 | 5 | 2 | 1430.210 | 1432.702 | 2.493 |
| 12 | 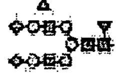 | 6 | 2 | 1494.731 | 1497.722 | 2.991 |
| 13 | 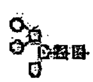 | 2 | 1 | 1579.783 | 1581.777 | 1.994 |
| 14 | 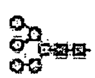 | 2 | 1 | 1783.883 | 1785.877 | 1.994 |
| 15 | 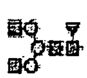 | 4 | 1 | 1835.925 | 1839.913 | 3.988 |
| 16 | 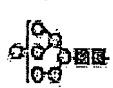 | 2 | 1 | 1987.883 | 1989.977 | 1.994 |

[M+2Na]²⁺: 1494.731 m/z (mono)

[M+Na]+: 1259.627 m/z (mono)

Figure 6

Table 1. IDAWG labeling efficiencies

| No. | N-linked glycan composition | Structure | Number of nitrogens | [M+Na]+ | | [M+2Na]2+ | | Labeling efficiency (%) |
| --- | --- | --- | --- | --- | --- | --- | --- | --- |
| | | | | m/z (mono) | Δ_M (m/z) | m/z (mono) | Δ_M (m/z) | |
| 1 | (Man)4+(Man)3(GlcNAc)2 | 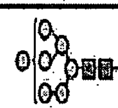 | 2 | 1887.983 | 1.994 | 1005.486 | 0.997 | 95 |
| 2 | (Man)5+(Man)3(GlcNAc)2 | 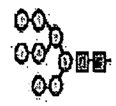 | 2 | 2192.082 | 1.990 | 1107.536 | 0.997 | 96 |
| 3 | (Gal)2(GlcNAc)2(Fuc)1+(Man)3(GlcNAc)2 | 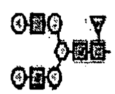 | 4 | 2244.125 | 3.988 | 1133.557 | 1.994 | 96 |
| 4 | (Gal)2(GlcNAc)2(Fuc)2+(Man)3(GlcNAc)2 | 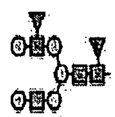 | 4 | 2418.214 | 3.988 | 1220.602 | 1.994 | 95 |
| 5 | (Gal)1(GlcNAc)3(Fuc)1+(Man)3(GlcNAc)2 | 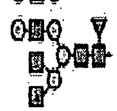 | 5 | 2285.152 | 4.985 | 1154.071 | 2.493 | 97 |
| 6 | (Gal)2(GlcNAc)3(Fuc)3+(Man)3(GlcNAc)2 | 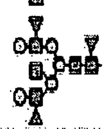 | 5 | 2837.430 | 4.985 | 1430.210 | 2.493 | 98 |

US 9,329,169 B2

VIVO ISOTOPIC LABELING METHOD FOR QUANTITATIVE GLYCOMICS

This application claims priority from U.S. provisional application Ser. No. 61/000,920, filed Oct. 29, 2007, entitled "IDAWG A novel quantitative method for glycomics-IDAWG", the entire contents of which application is incorporated by reference in its entirety herein.

This application is a U.S. National Stage of International Application No. PCT/US2008/012283 filed 29 Oct. 2010 and claims the benefit under 35 U.S.C. §119(e) of U.S. Provisional Patent Application No. 61/000,920 filed 29 Oct. 2007.

CLAIM OF PRIORITY AND GRANT SUPPORT

This invention was made with Government support under Grant Nos. NIH/NCRR 5P41RR018502 and NIH/NIDDK 1R01DK075069, awarded by the National Institutes of Health. Consequently, the U.S. Government has certain rights in this invention.

FIELD OF THE INVENTION

The present invention relates to a method of isotopically labeling glycans and in facilitating high throughput quantitative/comparative analysis of glycomic compositions of biological cells.

BACKGROUND OF THE INVENTION

A range of strategies have been developed for the high throughput quantitative/comparative analysis of large scale systems to enable the expression levels of various molecules to be compared between different biological states. In the—omics fields, the techniques used in the field of proteomics are probably the most developed, and can be broadly subdivided into two general schemes—those that involve the use of labels and those methods that are label free. In the label free approaches, various aspects of the peptides/proteins such as normalized ion intensities, spectral counts, mass, scan number and signal intensity, and accurate mass plus retention time have been successfully used to assign the protein expression level for comparative investigations[1-4]. However, the ionization efficiency of each analyte depends on factors such as its molecular mass, proton/cation affinity, surface activity, the presence of other compounds which compete with or interfere with the ionization of the analyte, etc., and thus the intensities of the ions do not directly correlate with concentration. In addition, the instrument's response can vary over time, so that the direct comparison of data from two or more analyses can yield dramatically different results. The alternative strategy for relative quantification overcomes these issues by simultaneously analyzing pairs of isotopically labeled populations, which offers the advantage that the heavy and light labeled peptide pairs are analyzed under exactly the same conditions, allowing a direct comparison of relative abundances for that peptide. Relative quantification between the isotopically labeled populations is performed by taking a ratio of the area or the intensity of the light and heavy monoisotopic peaks.

Numerous strategies have been developed for introduction of a stable isotope into populations of proteins[5-12]. For example, isotope-coded affinity tags (ICAT) chemically target specific amino acids, typically cysteine, in the peptide sequence for differential labeling[5]. Other in vitro approaches also target functional groups of the polypeptides[6, 8-12]. Stable isotopes can also be introduced into biological systems via metabolic labeling. For instance, stable isotope labeling with amino acids in cell culture (SILAC) provides a simple and straightforward method for the in vivo incorporation of an isotopic label into proteins prior to MS based proteomics[7]. In a SILAC experiment, two cell populations are grown in culture media that are identical except that one of them contains a "light" and the other "heavy" forms of particular amino acids ($^{12}$C and $^{13}$C labeled lysine and arginine for example). The labeled analogs of amino acids are supplied to cells in culture instead of the natural amino acids, and it becomes incorporated into all newly synthesized proteins. After a number of cell divisions, each instance of the particular amino acids is replaced by its isotope labeled analog. An advantage of this approach, over the in vitro approaches, is that the cells are mixed together immediately after cell lysis. Thus, proteins from both cell types are subjected to the exact same experimental conditions during sample handling, digestion, purification, etc., which eliminates the differential losses that can occur when the samples are treated separately in a parallel manner. For this reason, SILAC is often considered the "gold standard" for quantitative proteomic analyses[13].

The field of comparative glycomics is not as mature as proteomics; however several of the quantitative proteomic tools have been adapted for glycomic analysis. For instance, total ion mapping (TIM) is a label free method that determines the prevalence, percent of an individual glycan to the total of all glycans in the sample, based upon the sum of the fragment ions intensities, and is in some ways similar to the label free methods used in proteomics[14]. In vitro isotopic labeling has also been developed by a number of groups. For N-linked glycans and free oligosaccharides, several isotope containing tags have been derived to label the reducing terminus[15-18]. O-linked glycans are usually released from the protein backbone via β-elimination, and thus are not amenable to these approaches. However, a quantitative method relying on β-elimination to introduce a mass label into the glycan has been developed[19]. Another proposed method for comparative isotopic labeling of oligosaccharides relies on heavy methyl iodide ($^{13}$CH$_3$, $^{12}$CDH$_2$, $^{12}$CHD$_2$, and/or $^{12}$CD$_3$) vs. light methyl iodide ($^{12}$CH$_3$) labeling during standard permethylation, which is a commonly used derivatization procedure prior to MS analysis of both N-linked and O-linked glycans[14, 20, 21]. In addition, an isobaric labeling strategy using permethylation with $^{13}$CH$_3$ and $^{12}$CDH$_2$ has been developed for both N- and O-linked glycans, and is particularly useful for the quantification of individual glycans present in isomeric mixtures[22, 23]. All of these in vitro approaches are useful tools for glycomics.

BRIEF DESCRIPTION OF THE FIGURES

FIG. 6 shows Table 1, which indicates the high labeling efficiencies of $^{15}$N labeling into N-glycans pursuant to the present invention as described herein.

SUMMARY OF INVENTION

Figure 1A:
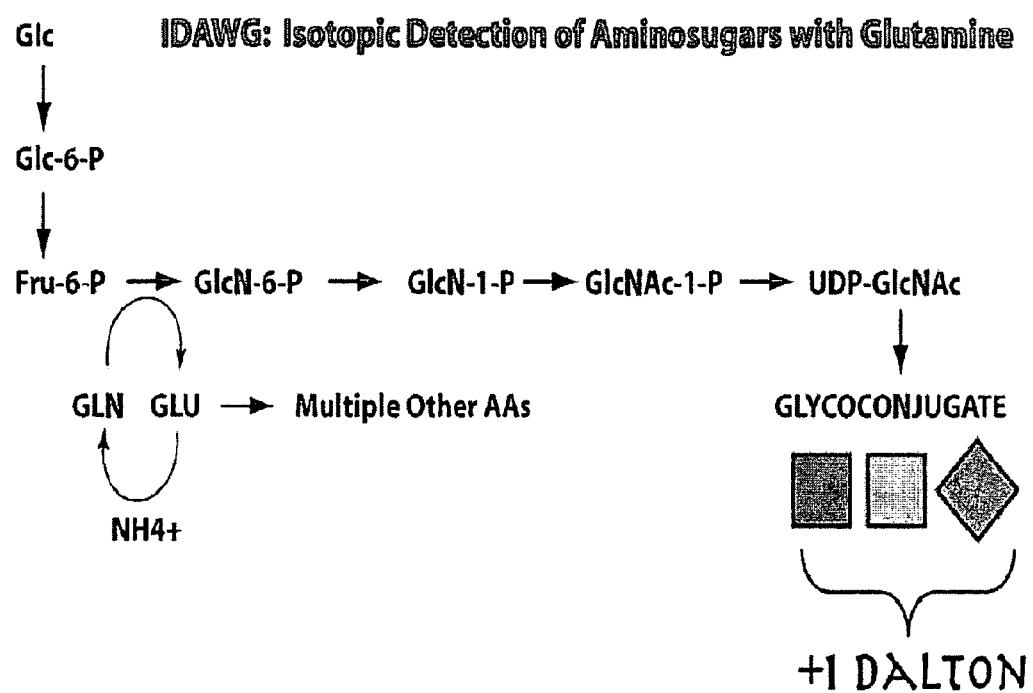
FIG. 1A is a schematic showing the hexosamine biosynthetic pathway which converts the glycolysis intermediate fructose-6-phosphate into UDP-GlcNAc.

This invention relates to a method for isotopic labeling of glycans. The method is useful in facilitating high throughput quantitative/comparative analysis of glycomic compositions of biological matter, especially including cells and tissue.

The present invention is directed to a methodology that takes advantage of stable isotope ($^{15}$N) labeling of glycans in cell culture for performing relative quantitative glycomics. This methodology, termed isotopic detection of aminosugars with glutamine (IDAWG), relies on the hexosamine biosynthetic pathway that uses the side-chain of glutamine as its sole donor source of nitrogen for aminosugars in the production of sugar nucleotides. Thus, for example, introduction of heavy glutamine ($^{15}$N) (as monomeric, dimeric or polymeric glutamine and their pharmaceutically acceptable salts) into otherwise Gln-free media allows for all aminosugars to become labeled and shifted in mass by +1 dalton.

The present invention is directed to a system for heavy (isotope) labeling of glycoconjugates in cell or tissue culture to facilitate quantitative glycomics. The methodology relies on the fact that the vast majority of cell or tissue culture systems require the addition of endogenous Gln and that Gln is the sole nitrogen donor for aminosugars via the hexosamine biosynthetic pathway. Thus, it was postulated and shown that if heavy Gln with $^{15}$N on the side chain (amide group) is used in the media, glycoconjugates containing GlcNAc, GalNAc, and sialic acids rapidly incorporate a heavy nitrogen into each of these monosaccharides. The cells, tissue and other biological material grown in heavy glutamine are then be isolated, extracted, etc. to obtain peptides and lipids which contain glycans, which are analyzed quantitatively and qualitatively. The method can be used to look at glycan ½ lives, perform relative quantification between two cell or tissue culture samples, and aids in glycan detection, characterization (type of glycan and optionally, peptide or lipid to which glycan is conjugated) and validation. Thus, using the present method, the impact of differentiation, disease or condition, drug, hormone or environmental factors on the quantity and quality of glycans can be measured and used diagnostically or therapeutically to identify changes in glycans during differentiation processes, to diagnose disease states, to monitor therapies and to measure drug, hormone and environmental activity on biological material, especially cells and tissue in culture.

Thus, the present invention relates to a method for accurately comparing the levels of glycans in biological material, especially cells and tissue, using mass spectrometry and isotopic labeling and optionally, nuclear magnetic resonance ($^{15}$N is paramagnetic) of biological material, especially glycosyl groups (glycans) on proteins and lipids with $^{15}$Gln.

In one aspect, the present invention allows for rapid and nearly complete incorporation of $^{15}$N into GlcNAc, GalNAc, and sialic acids of N-Linked and O-linked glycans in various mammalian cell and tissue culture systems. Besides aiding in the assignment of structures (local on peptides or lipids and structures of glycans) via LC-MS$^n$ and optionally, NMR approaches, this method allows a determination whether the glycans isolated from a sample result from cellular processes or serum glycoproteins. Importantly, this method also allows a comparison in a quantitative manner of the glycans between two cell populations. Furthermore, half-life studies can be performed on glycan structures by switching a cell population from heavy to light labeling conditions and harvesting and analyzing the glycans by LC-MS$^n$ approaches at multiple time points afterwards. Thus, the present invention is an easily applied and powerful new tool in the glycomics toolbox. It is noted that because $^{15}$N is a paramagnetic atom, the analysis with mass spectrometry may be complemented with NMR studies focusing on $^{15}$N.

As glycosylation plays a major role in multiple physiological and pathophysiological processes the application of the present invention is quite broad and includes the following methods, inter alia:

1. defining and quantifying changes in the glycome/glycoproteome following embryonic/adult stem cell differentiation or any other type of differentiation (preadipocytes to adipocytes, neuronal progenitor differentiation, etc.) This approach has particular applicability in differentiation processes and can be used to enhance methods and production of various multipotent stem and progenitor cells and various precursor cells, including the use and inclusion of particular types and concentrations of differentiation agents;

2. defining quantifying and/or qualifying changes in the glycome/glycoproteome upon disease progression (the induction of insulin resistance (type II diabetes), oncogenesis and metastatic potential (cancer), etc.). This aspect may be particularly useful for diagnosing a disease or monitoring the progression of a disease state, including metabolic syndrome, diabetes I and II, obesity, cardiovascular disease and damage, neurodevelopmental diseases, neurological diseases including Alzheimer's disease and Parkinson's disease, among others;

3. defining and quantifying changes in the glycome/glycoproteome upon drug/small molecule treatment. This aspect may be particularly useful for assaying drug potencies as inhibitors/agonists/modulators of cellular activity and biological function and that activity and function relate to glycan production;

4. defining and quantifying changes in intracellular glycosylation of proteins (O-GlcNAc) that has been shown to be involved in type II diabetes, tauopathies such as Alzheimer's and Parkinson's disease, cardiovascular injury, etc. This aspect may be particularly use for determining appropriateness of therapeutic intervention in a number of disease states/conditions;

5. defining and quantifying changes in the glycome/glycoproteome upon changes in culturing media or conditions (scale up for monoclonal antibody or recombinant protein production and related biological products and cellular samples).

The present invention thus provides one or more of the following:

1. stable isotope tagging in cell or tissue culture for performing relative quantification glycomic/glycoproteomics experiments (A vs B) (similar to SILAC for proteomics).

2. allows for in cell/tissue synthesized glycomic structures to be distinguished from glycans/glycoconjugates from media contamination.

3. allows for "pulse-chase" experiments to be performed to investigate half-life of glycan structures. This also can be used to determine the change in glycan structures over time under a number of conditions to provide insights into conditions which may influence the half-life of the glycan structures.

4. aids in the assignment of structure during glycan sequencing.

5. reduces glycomic efforts by quickly detecting differences between 2 samples (a simple full MS spectra) so that effort can be applied to characterizing only the structures that change.

6. Stable isotope difference is propagated into MSn analysis allowing for multiple peak pairs to be generated for a structure that aids in assigning the structure and allows for statistical relative quantification in $MS^n$ mode.

The present invention is directed to am in vivo labeling strategy for glycomic studies. More particularly, the invention contemplates the isotopic detection of aminosugars with glutamine and relies on the hexosamine biosynthetic pathway that uses the side-chain of glutamine as its sole donor source of nitrogen for aminosugars in the production of sugar nucleotides. Thus, introduction of glutamine with a $^{15}N$ labeled side-chain (amide-$^{15}$N-Gln) into Gln-free media allows for all aminosugars, including GlcNAc, GalNAc, and sialic acids, to become labeled with $^{15}N$. Through the incorporation of $^{15}N$ in this manner, the mass of N- and O-linked glycans, glycolipids, and extracellular matrix polysaccharides, which should all be increased by +1 Dalton units per aminosugar, may be measured and analyzed. Mass spectrometry data may be supplemented with NMR data inasmuch as $^{15}N$ is paramagnetic and is amendable to NMR studies. The present inventors demonstrate the utility of this approach by the analysis of both N-linked and O-linked glycans released from proteins of murine embryonic stem cells grown in both the light and amide-$^{15}$N-Gln. The success of these experiments presented herein clearly indicates that the present method is useful for a variety of comparative glycomic studies in cell culture.

The present invention provides a simple-to-implement but powerful isotopic labeling strategy for glycans in cell culture systems. The present method relies on the fact that the amide side chain of Gln is the sole nitrogen donor for UDP-GlcNAc via the hexosamine biosynthetic pathway and that UDP-GlcNAc is the substrate for the biosynthesis of UDP-GalNAc and CMP-Neu5Ac(Gc). Thus, the present inventors demonstrate, using mouse ES cells, that replacement of the normal Gln supplement with amide-$^{15}$N-Gln allows for nearly complete isotope labeling of GlcNAc, GalNAc, and NeuAc residues of N-linked and O-linked glycans within a 72 hour labeling strategy.

The present invention provides for robust quantification of glycans released from proteins and lipids between two samples. Furthermore, this technique provides a labeling strategy amenable for examining and quantifying glycopeptides directly. This strategy is demonstrated in examining the dynamic O-GlcNAc modification[30] on proteins isolated from light and heavy Gln-labeled cell culture systems. The observation that $^{15}$N-Gln also is incorporated into proteins, but no other heavy amino acids are observed as expected, provides a labeling strategy that may be used alone or in combination with heavy Arg/Lys SILAC[7] analysis to quantify glycans, proteins, and glycoproteins/glycopeptides all from the same set of samples. The present method may also be used to qualify glycosylation and to determine the binding sites of glycosyl groups on proteins and lipids. Finally, the present method enables calculation of the half-life of all aminosugar-containing glycans in a sample by completely labeling the sample first and then replacing the heavy Gln with light Gln at one or more intervals and isolating and analyzing samples over a time-course. Thus, the present method presents a powerful new quantitative and qualitative tool for exploring the biological role of glycans, glycoproteins, and glycolipids in cell culture systems.

In one embodiment of the present invention, a method for comparing the relative abundance of glycans in one or more samples of biological material, preferably cells or tissue including live cells is disclosed, wherein one of the samples has been modulated by exposure to a treatment, such as differentiation, a drug, hormone, bacteria or virus, or a stimulus, such as a chemical or environmental stimulus. In this aspect of the invention, a first sample of the biological material (especially, cells or tissue) is cultured in a first medium containing heavy glutamine ($^{15}$N glutamine) and a second sample of the biological matter is cultured in a second medium containing light glutamine ($^{14}$N glutamine). One of the samples, preferably the sample which is exposed to heavy glutamine, is modulated, the sample is then lysed, extracted to remove proteins and/or lipids and the proteins and/or lipids which remain (not extracted) are optionally further separated into proteins and/or lipids which contain glycans and then exposed to PNGaseF treatment and β-elimination to release glycans from the proteins and/or lipids which are contained in the sample. Proteins and/or lipids may be removed from the glycans using standard methods available in the art including liquid chromatography (e.g. reverse phase HPLC) and the glycan sample is then analyzed by mass spectrometry and optionally NMR, to determine the quantity and type of glycan which is found in the sample. The same process is performed for the control sample and the resulting analysis performed (primarily MS, but optionally, NMR if heavy glutamine, rather than light glutamine is used to contact the control sample during growth) and the glycans are quantified and qualified. The results obtained for the modulated sample is compared to the results obtained for control sample to determine the impact modulation has had on glycan quantities and qualities.

As indicated, modulation can take the form of differentiation of a precursor cell to a more mature cell to determine the impact of differentiation on glycan content and type, the effect (diagnosis) of a disease state or abnormal condition on cells or tissue, the impact of a drug or other small molecule on a cell (normal, diseased or exhibiting a condition) for purposes of determining activity of the drug or small molecule, monitoring of therapy in a diseased or abnormal cell (exhibiting a condition to be treated) comparison to a normal, control cell and determining the impact of culture conditions on the production of cells pursuant to a manufacturing process.

As indicated, it is also possible to culture each sample in heavy glutamine so as to provide not only a facility for performing mass spectrometry on glycan residues, but also to provide further information related to glycan structure of both the modulated biological material, as well as the control.

The analysis of glycans can proceed on the isolated glycans or on the proteins or lipids to which the glycans are bound. Thus, in this aspect, smaller samples of the modulated biological material and/or control material may be separated from the remaining sample and the proteins or lipids containing glycan may be analyzed directly by $MS^n$ and optionally NMR to provide information related to the type and amount of glycan bonded to a protein and/or lipid and the protein and/or lipid to which the glycan is bound. A further aspect of the invention involves exposing the protein or lipid to digestion using, for example, proteases or lipases prior to $MS^n$ analysis and optionally NMR analysis, in order to determine the glycan-protein or glycan-lipid binding site.

As discussed, the glycans are released from the protein and/or lipid, which is optionally digested using techniques which are standard in the art (e.g., PNGaseF treatment and β-elimination for N- and O-linked glycans, respectively). The released glycans are then analylzed using $MS^n$ (e.g., linear ion trap mass spectrometer or hybrid linear ion trap mass spectrometer) and optionally NMR analysis. Total content of glycans is determined and/or structural determination of glycan structures is then made using standard methods available in the art (e.g. fragmentation rules and glycoworkbench (see dkfz-heidelberg.de/spec/EUROCarbDB/GlycoWorkbench/ as well as NMR analysis). In addition, the proteins and/or polypeptides and lipids upon which glycosylation occurs may also be determined using this (determining the polypeptides and/or lipids bound to glycosyl groups from the mass spec analysis) and similar techniques (such as, for example, separating out all lipids and proteins which have glycosidic linkages from those which do not have glycosidic linkages and then identifying the proteins, polypeptides and lipids within that population). The results obtained are then compared to the results obtained for a control population, which, depending upon the objective of the analysis, may represent a control cell population otherwise identical to the analyzed cell population grown in light glutamine containing cell media, or alternative, the control population may be one or more of a precursor population, a normal cell population (in the event disease states are to be looked at) or other population which is grown in the presence or absence of heavy glutamine. Depending upon the control population and cell growth conditions used, the glycosidic content is also obtained for the control population and then compared to the modulated population.

Alternatively, and preferably, the samples (modulated sample and control) may be combined and the same procedure may be used on the combined samples such that glycosylated proteins and/or glycosylated lipids are collected/separated, optionally digested, and exposed to $MS^n$ and optionally, NMR to provide information related to the extent, type and binding sites of glycans on proteins and/or lipids. In this aspect of the invention, the modulated sample or control sample (preferably, the modulated sample) is grown in the presence of heavy glutamine and the other sample is grown in the presence of light glutamine, the samples are combined and analysis of the combined sample proceeds as described hereinabove. Using this methodology, experimental throughput is enhanced considerably and the MS data which is generated can provide isotope ratios which will allow a direct comparison between the modulated sample and the control sample in a single combined (pooled), and analyzed sample.

In certain aspects of the invention, the isolated proteins or lipids, which may or may not be digested, are subjected to mass spectroscopy to develop a mass spectrum. The difference in the mass of the isotope in the cell pool results in two distinct, closely spaced peaks for each protein, peptide, lipid and/or glycan in the mass spectrum (depending upon how the sample has been processed). One peak in the mass spectrum corresponds to a protein, peptide, lipid or glycan from the pooled samples with normal isotopes (light glutamine). The other peak corresponds to a protein, peptide, lipid and/or glycan from the sample enriched in heavy glutamine. A ratio is computed between the peak intensities of at least one pair of peaks in the mass spectrum. The relative abundance of the glycan (bound to protein, peptide or lipid or released from the protein, peptide or lipid) in each sample may be determined based on the computed ratio. The glycan may be identified by the mass-to-charge ratios of the peaks in the mass spectrum, as well as by other means known in the art, especially including NMR analysis.

Thus, the effects of two samples can be simultaneously analyzed by preparing additional samples with media containing heavy glutamine, and modulating and analyzing the additional samples. Up to the point of the mass spectroscopy, none of the steps of the process discriminates between a glycan which contains heavy glutamine from a glycan which contains light glutamine. Thus, the ratios of the original amounts of glycans from the two samples are maintained, normalizing for differences between extraction and separation of the proteins in the samples.

Although the identification of structures from released, permethylated glycans is well established, the present invention allows increased confidence in the identification since the observed shift in m/z between light and heavy fragments must correspond to the number of nitrogens in the proposed structure. Also, confidence is gained in the tandem MS/MS spectra following collision-induced disssocation in that assigned fragment ions from light and heavy samples must also contain the correct number of nitrogens based off the m/z shift to be correct. Finally, comparing the spectra from heavy and light allows one to delineate intact glycans in full MS spectra and fragmentation spectra from noise for those glycans or glycan fragments containing an aminosugar.

DETAILED DESCRIPTION OF THE INVENTION

The following terms are used to define the present invention. In instances where a term is not specifically defined herein, the term shall be accorded the meaning, in context as applied to one or more aspects of the present invention, to which one of ordinary skill would apply.

Unless otherwise noted, the terms used herein are to be understood according to conventional usage by those of ordinary skill in the relevant art. In addition to the definitions of terms provided below, definitions of common terms in molecular biology and biochemistry may also be used for example as found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The term "patient" or "subject" is used in context to describe an animal, including a human for whom a therapy, diagnosis or other feature of the present invention may be provided or may be relevant.

The term "biological material", "cells" and "tissue" are used to describe a culture of biological cells or tissue, including in particular, human cells, microbiological cells in culture, tissue, an organ, and may include tissue which is obtained from a whole animal for purposes of diagnosis. In preferred aspects, biological material is primarily cells or tissue which is grown in culture.

The term "modulation" is used to describe non-control experimental conditions for which an analysis and impact on biological material is to be determined using the present invention. Modulation conditions are contrasted with control conditions. Modulation conditions may include exposing cells to differentiation conditions, drugs, hormones, environmental conditions, disease states and abnormal conditions in order to assess the impact of modulation on the glycomics of the cell compared to a normal cell. A "modulated" biological sample or "modulated cells or tissue" are those cells or tissue which are exposed to experimental (non-control) conditions in order to assess the impact of those conditions on cells in comparison to a control sample. A "modulating agent" is an agent which is typically added to a culture medium in order to modulate said cells as otherwise described herein. The modulating agent may be a differentiation agent(s), a drug, a hormone, another chemical including a suspected toxin, environmental conditions, manufacturing conditions, or an agent such as a microbe which causes a disease state.

The term "glycosylation" is used to describe a process in which the formation of linkages with glycosyl groups occurs on proteins (polypeptides) and lipids. "N-linked glycosylation" is based on the attachment of oligosaccharides, generally (though not exclusively) synthesized on a dolichol-lipid platform to proteins through the amino acid asparagine spaced close to threonine or serine in the polypeptide sequence.

In contrast, O-linked glycosylation is based upon the attachment of groups of oligosaccharides directly to proteins through the hydroxyl group of serine or threonine.

Glycosylation is the process or result of addition of saccharides to proteins and lipids. The process is one of four principal co-translational and post-translational modification steps in the synthesis of membrane and secreted proteins and the majority of proteins synthesized in the rough ER undergo glycosylation. It is an enzyme-directed site-specific process, as opposed to the non-enzymatic chemical reaction of glycation. As discussed above, two types of glycosylation exist: N-linked glycosylation to the amide nitrogen of an asparagine side chains and O-linked glycosylation to the hydroxy oxygen of serine and threonine side chains.

The polysaccharide chains attached to the target proteins serve various functions. For instance, some proteins do not fold correctly unless they are glycosylated first. Also, polysaccharides linked at the amide nitrogen of asparagine in the protein confer stability on some secreted glycoproteins. Some experiments have shown that glycosylation in this case is not a strict requirement for proper folding, but the unglycosylated protein degrades quickly. Glycosylation may play a role in cell-cell adhesion (a mechanism employed by cells of the immune system), as well as in differentiation processes.

There are various mechanisms for glycosylation, although all share several common features. Glycosylation is an enzymatic process, the donor molecule is an activated nucleotide sugar and the process is site-specific.

N-linked glycosylation is important for the folding of some of eukaryotic proteins. The N-linked glycosylation process occurs in all eukaryotes. For N-linked oligosaccharides, a 14-sugar precursor (dolichol) is first added to the asparagine in the polypeptide chain of the target protein. The structure of this precursor is common to most eukaryotes, and contains 3 glucose, 9 mannose, and 2 N-acetylglucosamine molecules. A complex set of reactions attaches this branched chain to a carrier molecule called dolichol, and then it is transferred to the appropriate point on the polypeptide chain as it is translocated into the ER lumen.

There are two major types of N-linked saccharides: high-mannose oligosaccharides, and complex oligosaccharides. High-mannose is, in essence, just two N-acetylglucosamines with many mannose residues, often almost as many as are seen in the precursor oligosaccharides before it is attached to the protein.

Complex oligosaccharides are so named because they can contain almost any number of the other types of saccharides, including more than the original two N-acetylglucosamines. Proteins can be glycosylated by both types of oligos on different portions of the protein. Whether an oligosaccharide is high-mannose or complex is thought to depend on its accessibility to saccharide-modifying proteins in the Golgi. If the saccharide is relatively inaccessible, it will most likely stay in its original high-mannose form. If it is accessible, then it is likely that many of the mannose residues will be cleaved off and the saccharide will be further modified by the addition of other types of group as discussed above.

The oligosaccharide chain is attached by oligosaccharyl-transferase to asparagine occurring in the tripeptide sequence Asn-X-Ser or Asn-X-Thr, where X could be any amino acid except Pro. This sequence is known as a glycosylation sequon. After attachment, once the protein is correctly folded, the three glucose residues are removed from the chain and the protein is available for export from the ER. The glycoprotein thus formed is then transported to the Golgi where removal of further mannose residues may take place. However, glycosylation itself does not seem to be as necessary for correct transport targeting of the protein, as one might think. Studies involving drugs that block certain steps in glycosylation, or mutant cells deficient in a glycosylation enzyme, still produce otherwise-structurally-normal proteins that are correctly targeted, and this interference does not seem to interfere severely with the viability of the cells. Mature glycoproteins may contain a variety of oligomannose N-linked oligosaccharides containing between 5 and 9 mannose residues. Further removal of mannose residues leads to a 'core' structure containing 3 mannose, and 2 N-acetylglucosamine residues, which may then be elongated with a variety of different monosaccharides including galactose, N-acetylglucosamine, N-acetylgalactosamine, fucose and sialic acid.

O-linked glycosylation occurs at a later stage during protein processing, probably in the Golgi apparatus. This is the addition of N-acetyl-galactosamine to serine or threonine residues by the enzyme UDP-N-acetyl-D-galactosamine: polypeptide N-acetylgalactosaminyltransferase (EC 2.4.1.41), followed by other carbohydrates (such as galactose and sialic acid). This process is important for certain types, of proteins such as proteoglycans, which involves the addition of glycosaminoglycan chains to an initially unglycosylated "proteoglycan core protein." These additions are usually serine O-linked glycoproteins, which seem to have at least one of two main functions. One function involves secretion to form components of the extracellular matrix, adhering one cell to another by interactions between the large sugar complexes of proteoglycans. The other main function is to act as a component of mucosal secretions, and it is the high concentration of carbohydrates that tends to give mucus its "slimy" feel. Proteins that circulate in the blood are not normally O-glycosylated, with the exception of certain types of antibodies (IgA1 and IgD) and C1-inhibitor.

O-fucose is added between the second and third conserved cysteines of EGF-like repeats in the Notch protein, and possibly other substrates by GDP-fucose protein O-fucosyltransferase 1, and to Thrombospondin repeats by GDP-fucose protein O-fucosyltransferase 2. In the case of EGF-like repeats, the O-fucose may be further elongated to a tetrasaccharide by sequential addition of N-acetylglucosamine (GlcNAc), galactose, and sialic acid, and for thrombospondin repeats, may be elongated to a disaccharide by the addition of glucose. Both of these fucosyltransferases have been localized to the endoplasmic reticulum, which is unusual for glycosyltransferases, most of which function in the Golgi apparatus. O-glucose is added between the first and second conserved cysteines of EGF-like repeats in the Notch protein, and possibly other substrates by an unidentified O-glucosyltransferase.

O—N-acetylglucosamine (O-GlcNAc) is added to serines or threonines by O-GlcNAc transferase. O-GlcNAc appears to occur on serines and threonines that would otherwise be phosphorylated by serine/threonine kinases. Thus, if phosphorylation occurs, O-GlcNAc does not, and vice versa. This is an important finding because phosphorylation and/or dephosphorylation has become an important indicator for the regulation of signaling within cells.

Another form of glycosylation is the GPI anchor. This form of glycosylation functions to attach a protein to a hydrophobic lipid anchor, via a glycan chain. (see also prenylation) very often on the cell surface.

The term "aminosugar" as used herein refers broadly to any sugar that contains an amino group in place of a hydroxyl group. Derivatives of amine-containing sugars, such as N-acetylglucosamine and sialic acid, while not precisely containing an amine, may also be considered amino sugars. The term "aminosugar" as used herein may specifically refer to a monosaccharide with an amino or substituted amino group in place of a nonglycosidic hydroxyl group. Aminosugars include, glucose-N-acetyl (GlcNAc), galactose-N-acetyl (GalNAc) and sialic acid are representative aminosugars in the present invention.

The term "glycan" or "glycosyl" is used herein to denote a polysaccharide or an oligosaccharide. The term "glycan" or "glycosyl" is also be used herein to refer to the carbohydrate portion of a glycoconjugate, such as a glycoprotein, a glycolipid, or a proteoglycan. Glycans can be homo or heteropolymers of monosaccharide residues and can be linear or branched.

The term "glycoconjugate" as used herein refers to carbohydrates that are covalently linked with other chemical species. In glycoproteins or proteoglycans, the glycans are liked to proteins, or polypeptides. In glycolipids or lipopolysaccharaides, glycans are linked to lipids.

The term "glycomics" as used herein denotes the systematic study of all glycan structures or glycomes (the entire complement of sugars, whether free or present in more complex molecules, of an organism) of a given cell type or organism, including genetic, physiologic, pathologic, and other aspects. Glycomics, an analogous term to genomics and proteomics, is the comprehensive study of "glycomes" (the entire complement of sugars, whether free or present in more complex molecules, of an organism), including genetic, physiologic, pathologic, and other aspects. Glycomics "is the systematic study of all glycan structures of a given cell type or organism". The identity of the entirety of carbohydrates in an organism is thus collectively referred to as the glycome.

The term "effective amount" is used throughout the specification to describe concentrations or amounts of components which are used in context in the present invention to produce an intended result. Effective amounts of components are those which are generally known to those of ordinary skill in the art and are typically used in the methods of the present invention. In one aspect of the present invention, an effective amount of isotopically labeled glutamine, is that amount of glutamine (about 0.1 to about 10 mM or more, preferably about 0.5 to 5 mM, about 1 to about 3 mM, about 2 mM) which is included in media in which cells to be analyzed are grown in amounts effective to isotopically label aminosugars on glycosyl groups of proteins and/or lipids for purposes of analysis. In general, cells are cultured from about 18-24 hours (less than 1 day) to about 1 day to about 14 days or more, about 24 hours to about 5 days (120 hours), for about 36 hours to about 96 hours, from about 48 hours to about 84 hours, from about 60 hours to about 72 hours.

In preferred aspects, high isotopic enrichment of $^{15}$N-glutamine is preferred. The medium which is enriched in $^{15}$N to a level of about 90-100% is preferred, with 100% enrichment most preferred.

The term "cell medium" or "cell media" are terms used to describe a cellular growth medium in which cells to be analyzed according to the present invention are produced, stabilized (grown) or alternatively, are differentiated into one or more intermediate or mature cells from a pluripotent or other precursor cell, e.g., a stem cell (such as a human embryonic stem cells, an adult stem cell or other cell) a progenitor cell or other cell or a differentiated cell. Cell media which may be used in the present invention are well known in the art and preferably comprise at least a minimum essential medium plus optional components such as growth factors, retinoic acid, glucose, non-essential amino acids, salts (including trace elements), glutamine ("light" or "heavy"), insulin (where indicated and not excluded), transferrin, beta mercaptoethanol, and other agents well known in the art and as otherwise described herein. Cell media which may be used includes cell media which contains between 2% and 20% (preferably, about 10%) fetal calf serum, or for defined medium an absence of fetal calf serum and KSR, but including for example, bovine serum albumin).

Any number of cell media may be used and are well known in the art. Depending upon the type of cells to be grown, stabilized and/or differentiated, the components are varied in order to maximize the desired outcome. DMEM/F12 is a preferred cell media which is often used for differentiation and or growth of stem and/or pluripotent cells. It contains 10% FCS. A large number of other cell media may also be used in the present invention. Cell media useful in the present invention are commercially available and can be supplemented with commercially available components, available from Invitrogen Corp. (GIBCO), Cell Applications, Inc. and Biological Industries, Beth HaEmek, Israel, among numerous other commercial sources. In preferred embodiments where precursor cells are differentiated, at least one differentiation agent such as one or more growth factors, retinoic acid, synthetic agents such as LY294002, among numerous others are added to the cell media in which a stem cell, progenitor or other precursor cell is grown in order to promote differentiation of the stem cells into progenitor cells and the progenitor cells into pancreatic endoderm cells or liver cells or stem cells into pancreatic endoderm cells or liver cells. One of ordinary skill in the art will be able to readily modify the cell media to produce progenitor or pancreatic/liver cells pursuant to the present invention. Cell differentiation medium is essentially synonymous with and subsumed under cell media but is used within the context of a differentiation process and includes cell differentiation agents to differentiate cells into other cells. Stabilizing medium is a type of cell medium which is used either before or after a differentiation step in order to stabilize a cell line for further use and is sometimes, but not always, identical to cell media in which cells are generally grown. In general, as used herein, cell differentiation medium and stabilizing medium may include essentially similar components of a cell medium, but are used within different contexts and may include different components in order to effect the intended result of the use of the medium.

The cells, especially during differentiation, may be grown on a cellular support, including, example, an extracellular matrix protein, such as laminin, tenascin, thrombospondin, and mixtures thereof, as well as other differentiation proteins which may be used in the present invention include for example, collagen, fibronectin, vibronectin, polylysine, polyornithine and mixtures thereof. In addition, gels and other materials which contain effective concentrations of one or more of these differentiation proteins may also be used. Exemplary embryonic stem cell differentiation proteins or materials which include these differentiation proteins include, for example, BD Cell-Tak™ Cell and Tissue Adhesive, BD™ FIBROGEN Human Recombinant Collagen I, BD™ FIBROGEN Human Recombinant Collagen III, BD Matrigel™ Basement Membrane Matrix, BD Matrigel™ Basement Membrane Matrix High Concentration (HC), BD™ PuraMatrix™ Peptide Hydrogel, Collagen I, Collagen I High Concentration (HC), Collagen II (Bovine), Collagen III, Collagen IV, Collagen V, and Collagen VI, among others.

As used herein when referring to a cell, cell line, cell culture or population of cells, the term "isolated" refers to being substantially separated from a source of cells such that a particular type of cell, cell line, cell culture, or population of cells are purified. In addition, the term "isolating" is used to refer to the physical selection of one or more cells out of a group of two or more cells, wherein the cells are selected based on cell morphology and/or the expression of various markers.

As used herein, the term "contacting" or "exposing" (i.e., contacting or exposing a cell with a compound and in particular, isotopically or non-isotopically labeled glutamine in cell culture) is intended to include incubating the compound and the cell together in vitro (e.g., adding the compound to cells in culture such as in adherent culture, or in suspension culture).

The term "isotopically labeled glutamine" or "heavy glutamine" refers to glutamine, or a pharmaceutically acceptable salt thereof, which is labeled in the amide position with $^{15}N$ (see below). Non-isotopically labeled glutamine or "light glutamine" refers to glutamine which is natural or non-isotopically labeled. In the present invention, the term heavy glutamine shall mean a population of glutamine molecules which are substantially (i.e., at least about 85-90%, at least abut 92%, at least about 95%, at least about 96%, at least about 98%, at least about 99% and approaching 100% by weight heavy glutamine. In preferred aspects, the amount of light glutamine in a heavy glutamine sample is no more than a small percentage by weight-generally less than about 2% by weight-substantially free of light glutamine. In the case of light glutamine, this term refers to a population of glutamine molecules which contains no more than a naturally occurring amount of heavy glutamine and generally less than 5%, less than 4%, less than 2% heavy glutamine.

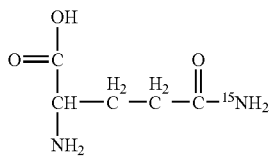

The present invention relates to the discovery that incubating biological material, including cells and/or tissue in a culture medium which comprises an effective amount of isotopically labeled glutamine for a period of at least about 18 hours (about 24 hours, about 36 hours, about 48, about 60 hours, about 72 hours, about 84 hours, about 96 hours, about 108 hours, about 120 hours or more, preferably between about 48 hours and 96 hours, about 72 hours) will result in metabolic labeling to incorporate a stable isotope or nitrogen, $^{15}N$ into the glycans of cells grown in culture.

The present invention is thus directed to a methodology that takes advantage of stable isotopic labeling of glycans in cell culture for performing relative quantitative glycomics. The present invention relies on the hexosamine biosynthetic pathway that uses the side-chain of glutamine as its sole donor source of nitrogen for aminosugars in the production of sugar nucleotides. Thus, for example, introduction of heavy glutamine ($^{15}N$) (as monomeric, dimeric or polymeric glutamine and their pharmaceutically acceptable salts) into otherwise Gln-free media allows for all aminosugars to become labeled and shifted in mass by +1 dalton.

The present invention relates to a method for heavy (isotope) labeling of glycoconjugates in cell culture to facilitate quantitative glycomics—to be used for glycoconjugates. The methodology relies on the fact that the vast majority of cell culture systems require the addition of endogenous glutamine (Gln) and that Gln is the sole nitrogen donor for aminosugars via the hexosamine biosynthetic pathway. Thus, it has been determined that when heavy Gln with $^{15}N$ on the side chain (amide) is used in the culture media, glycoconjugates containing GlcNAc, GalNAc, and sialic acids rapidly incorporate a heavy nitrogen into each of these monosaccharides. The method can be used to look at glycan ½ lives, perform relative quantification between two cell culture samples, and aids in glycan detection, characterization and validation, especially as it relates to the impact of glycan change in cells during differentiation, including the impact of change in glycan composition as cells mature. The method is also useful for analyzing the impact of cellular glycosylation on disease states and disease progression.

In one aspect, the present invention allows for rapid and nearly complete incorporation of $^{15}N$ into GlcNAc, GalNAc, and sialic acids of N-Linked and O-linked glycans in various mammalian cell culture systems. Besides aiding in the assignment of structures via liquid chromatography/mass spectroscopy (LC-MS$^n$) approaches, this method allows us to determine whether the glycans isolated from a sample result from cellular processes or serum glycoproteins. Importantly, the present method allows a comparison in a quantitative manner the glycans between two cell populations. Furthermore, half-life studies can be performed on glycan structures by switching a cell population from heavy to light labeling conditions and harvesting and analyzing the glycans by LC-MS$^n$ approaches at multiple time points afterwards. Thus, the present method is an easily applied and extremely powerful new tool in the glycomics toolbox.

As glycosylation plays a major role in multiple physiological and pathophysiological processes the application of this technique is quite broad and includes the following methods, inter alia:

1. defining and quantifying changes in the glycome/glycoproteome following embryonic/adult stem cell differentiation or any other type of differentiation (e.g., progenitor cells to more mature cells emanating from the progenitor cells, preadipocytes to adipocytes, neuronal progenitor differentiation, etc.) This approach has particular applicability in differentiation processes and can be used to enhance methods and production of various multipotent stem and progenitor cells and various precursor cells;

2. defining quantifying changes in the glycome/glycoproteome upon disease progression, e.g., (the induction of insulin resistance (type II diabetes), oncogenesis and metastatic potential (cancer), etc.), as well as numerous other disease states such as Alzheimer's and Parkinson's disease and cardiovascular injury. This aspect of the present invention is particularly useful for diagnosing a disease or monitoring the progression of virtually any disease state where glycosylation is impacted;

3. defining and quantifying changes in the glycome/glycoproteome upon drug/small molecule treatment. This aspect may be particularly useful for assaying drug potencies as inhibitors/agonists/modulators of cellular activity and biological function;

4. defining and quantifying changes in intracellular glycosylation of proteins (O-GlcNAc) that has been shown to be involved in type II diabetes, tauopathies such as Alzheimer's and Parkinson's disease, cardiovascular injury, etc., This aspect may be particularly use for determining appropriateness of therapeutic intervention in a number of disease states/conditions;

5. defining and quantifying changes in the glycome/glycoproteome upon changes in culturing media or conditions (scale up for monoclonal antibody or recombinant protein production and related biological products and cellular samples). This aspects related to enhancing production capabilities of biologicals which occur within a cellular milieu.

The methods of the present invention provide one or more of the following:

1. stable isotope tagging in cell culture for performing relative quantification glycomic/glycoproteomics experiments (A vs B) (similar to SILAC for proteomics) in vivo.
2. allows for in cell synthesized glycomic structures to be distinguished from glycans/glycoconjugates from media contamination.
3. allows for "pulse-chase" experiments to be performed to investigate half-life of glycan structures.
4. aids in the assignment of structure during glycan sequencing.
5. reduces glycomic efforts by quickly detecting differences between 2 samples (a simple full MS spectra) so that effort can be applied to characterizing only the structures that change.
6. Stable isotope difference is propagated into MS$^n$ analysis allowing for multiple peak pairs to be generated for a structure that aids in assigning the structure and allows for statistical relative quantification in MS$^n$ mode.

There are several approaches for using the present method. For example, one approach will be to grow a cell population to be analyzed in heavy glutamine cell culture. After a period of time, the cells are collected, extracted, the proteins and/or lipids collected and subjected to peptide or lipid digestion. The glycans are released from the digested protein and/or lipid using techniques which are standard in the art (e.g., PNGaseF treatment and β-elimination for N- and O-linked glycans, respectively). The glycans are then analyzed using MS$^n$ (e.g., linear ion trap mass spectrometer or hybrid linear ion trap mass spectrometer) and optional NMR. Total content of glycans is determined and/or structural determination of glycan structures is then made using standard methods available in the art (e.g. fragmentation rules and glycoworkbench (see dkfz-heidelberg.de/spec/EUROCarbDB/GlycoWorkbench/). In addition, the proteins and/or polypeptides and lipids upon which glycosylation occurs may also be determined using this (determining the polypeptides and/or lipids bound to glycosyl groups from the mass spec analysis) and similar techniques (such as, for example, separating out all lipids and proteins which have glycosidic linkages from those which do not have glycosidic linkages and then identifying the proteins, polypeptides and lipids within that population). The results obtained are then compared to the results obtained for a control population, which, depending upon the objective of the analysis, may represent a control cell population otherwise identical to the analyzed cell population grown in light glutamine containing cell media, or alternatively, the control population may be one or more of a precursor population, a normal cell population (in the event disease states are to be looked at) or other population which is grown in the presence or absence of heavy glutamine. Depending upon the control population and cell growth conditions used, the glycosidic content is also obtained for the control population and then compared to the analyzed population.

Although the identification of structures from released, permethylated glycans is well established, the present invention allows increased confidence in the identification since the observed shift in m/z between light and heavy peaks must correspond to the number of nitrogens in the proposed structure. Also, confidence is gained in the tandem MS/MS spectra following collision-induced disssocation in that assigned fragment ions from light and heavy samples must also contain the correct number of nitrogens based off the m/z shift to be correct. Finally, comparing the spectra from heavy and light allows one to delineate intact glycans in full MS spectra and fragmentation spectra from noise for those glycans or glycan fragments containing an aminosugar.

In preferred aspects of the present invention, a modulated sample and a control sample are combined, processed and then analyzed using MS and optionally, NMR analysis. The various steps as described above are identical except that the control sample and modulated sample are combined prior to processing. Analysis with MS produces a spectrum which provides a ratio of heavy istopically labeled fragments to light isotopically labeled fragments and from these ratios, determinations can be made about the amount of glycosylation, type (structure) of glycans present and site of glycosylation (on a protein, peptide or lipid). NMR data, which is optionally applied, may provide further input into the glycomics analysis.

Differentiation

By way of example and without limitation, in a study which is performed to determine the impact on glycosidic content and the types of proteins and/or lipids glycosylated and the extent of glycosylation during differentiation from a precursor cell to a mature cell, a precursor cell is differentiated (modulated) to a mature cell in the presence of isotopically labeled glutamine containing cell media further containing differentiation agents. Control cells are prepared which are grown in identical media containing light glutamine and an absence of differentiation factors. The resulting differentiated cell is then analyzed as described above to determine the extent and type of glycosylation and optionally, the proteins, peptides and/or lipids upon which glycosylation occurs during the differentiation process. The results obtained for the differentiated cell are compared to the control cell which can be grown in the presence or absence of isotopically labeled glutamine and the resulting glycosylation analysis compared with that obtained for the differentiated cell, thus establishing an extent and type of glycosylation and the proteins, peptides and lipids which are glycosylated during differentiation. Preferably, the control cells and differentiated cells are combined, processed and analyzed together. The resulting MS$^n$ and optionally NMR analysis provides data sufficient to make determinations as to extent and type of increased/decreased glycosylation, the proteins, peptides and lipids which are differentially glycosylated and the sites of glycosylation on proteins, peptides and lipids from differentiated cells compared to precursor (undifferentiated control cells).

The above glycomics analysis may also be used to identify differentiation factors and/or cell media conditions which will enhance (e.g., purity and number of cells) the differentiation of precursor cells to more mature cells.

Disease Progression/Diagnosis

The present method may be used to determine the impact of a disease or abnormal condition on biological material (cells and/or tissue) by analyzing for glycomics changes in cells which progress to a disease state or abnormal condition. Cells or tissue which are in a disease state or exhibit an abnormal condition are grown in cell culture in the presence of heavy glutamine. A control cell (normal state with no disease or condition present) is also grown in identical media in the presence of light glutamine. After a sufficient period (as otherwise disclosed herein, preferably about 72 hours or more), each sample of cells is processed separately or preferably, combined as described hereinabove and analyzed ($MS^n$ and optionally, NMR) to determine the impact of the disease state or condition on the amount, type/structure of glycans and their binding (including sites of binding) to proteins, peptides and/or lipids. The results obtained provide markers which may be used to diagnose the presence of disease or an abnormal condition in a patient. The method can be used to diagnose disease by comparing a cell sample suspected of having a disease or an abnormal condition with a normal cell using the present method to provide glycomics analysis on each of the samples and comparing the results. The samples can be analyzed separately or combined and analyzed as otherwise described herein.

Drug Activity or Toxicity

The present method may also be used to determine the impact that a drug or small molecule may have on the glycomics of a cell or tissue sample to which cell or tissue is exposed. In this aspect of the invention, one or more cell samples are exposed to a drug or small molecule at a single concentration or varying concentrations in the presence of a culture media containing effective amounts of heavy glutamine. The control sample is grown in identical cell media in the absence of drug and which includes light glutamine. After a sufficient period (e.g., about 72 hours or as otherwise described herein), the samples are collected and processed as otherwise described. Each sample, including the control sample, may be analyzed for the influence that the drug at a tested concentration may play in influencing the cells or tissue's glycomics. Alternatively, a modulated cell sample (at a single drug concentration) may be combined with a control sample and processed as otherwise described herein to provide an indication of the impact of the drug concentration on the glycomics of the cell tested. The method can be used to test drugs and other small molecules for activity as well as potential toxicity to cells.

Manufacturing/Production Efficiency

The present method may also be used to identify components or conditions to determine a manufacturing process or to enhance manufacturing efficiency of cells or tissue, especially including cells or tissue which are to be differentiated and produced in significant numbers. In this method, a cell sample which is to be manufactured/differentiated is exposed to varying culture conditions (time, temperature, components of media, differentiation agents) in the presence of a culture media which contains heavy glutamine for a period consistent with manufacture (about 18 hours to several weeks or more, usually about 2-5 days, depending upon conditions) and compared with a control sample manufacture, e.g., a final cell population, including for example, a differentiated cell population produced from a precursor cell grown under standard differentiation conditions (known time, known components, known purity of final cells/tissue produced) but in the absence of differentiation agents or other components to be tested and in the presence of heavy glutamine. The modulated sample(s) are grown for varying periods of time (including the time to produce the control cells) and the modulated sample(s) (with tested components and conditions) is/are analyzed using the methods of the present invention at varying time intervals to determine the relative efficiency, degree of purity and efficiency of the production of differentiated product in comparison to the control sample. A number of modulated samples may be prepared to determine optimum manufacturing conditions for the cell/tissue product.

Glycan Half-Life

Another application of the present invention is the calculation of individual glycan half-lives. In this experiment, cells are labeled to completion (for a period ranging from about 24 hours to about 120 hours, preferably about 60-72 hours) with amide-15N-Gln, the cells analyzed at that point using the methods otherwise described herein to provide an indication of quantity and quality, including structural features of the glycan content of the cells at that point. The cells are thereafter switched to culture media containing only 14-N Gln. Aliquots of $^{14}N$ labeled cells are taken at various time points and mixed with fully-labeled $^{15}N$ cells to calculate the ratio of incorporation for each glycan structure as a function of time. By doing this at multiple time points and plotting the % incorporation versus time, the ½ life for each glycan in the cell can be calculated. This experiment can also be combined to calculate the half-life of glycans upon any perturbation to the cells such as transformation, differentiation, drug treatment, or any change in feeding conditions.

In general, cells to be analyzed for a change in glycosidic content compared with a control cell are cultured in heavy glutamine labeled with $^{15}N$. After a sufficient period of time, generally at least about 18 hours, but more particularly, approximately 60-72 hours or more, the cells are collected, lysed, the proteins extracted, separated/collected and then analyzed using $MS^n$ to determine total glycosidic content on the individual proteins (which may additionally be digested to provide glycosylated peptides, which can be measured). Total glycosidic content of the cells may be determined and compared with a control population of cells grown in media which does not contain heavy labeled glutamine.

The samples which are grown are preferably combined to provide a ratio for each fragment in one batch in order to enhance experimental throughput. In a preferred method according of the present invention, the modulated cell/tissue sample is grown in heavy glutamine containing culture medium and the control sample is grown in virtually identical culture medium as the modulate sample with the exception that light glutamine is used in the culture medium rather than heavy glutamine and additional components (e.g. differentiation agents, etc. which are the basis of the modulation made) also may be added to the modulated medium.

As discussed, it is preferred that the media the cell pools are grown in be identical, except for the presence of the heavy/light glutamine and modulators which are included in the modulated sample. Commercial suppliers may provide heavy glutamine containing culture meda (Cambridge Isotope Laboratories, Inc.). Alternatively, the cells may be grown in the same medium and the labeling isotope and modulator(s)) may be added directly to one culture of cells.

The modulated cell sample is modulated by differentiation agents, a microbe (bacteria/virus), a chemical, a drug, a hormone, or an environmental change, such as a temperature/concentration/time change, for example. Other treatments or stimulus may be provided, as well. The other sample to be measured functions as a control.

After processing of the biological material (samples), the glycosidic ratio (isotopic ratio) which is obtained from mass spec analysis will be an indication of the change in glycosylation between the cells to be analyzed (modulated cells) and the control cell population. MS analysis, alone or combined with NMR analysis may provide further information related to glycan structure, the proteins, peptides (after digestion of the proteins in the sample) and/or lipids which are bound to glycans and the binding sites of the glycan binding.

In a preferred method, after growth in cell culture for a sufficient period of time, modulated and control samples of the biological material are then combined. The proteins are extracted from the combined cell pool in a manner known in the art. For example, the cell membranes may be digested or disrupted by standard methods, such as detergents or homogenization in an isotonic sucrose solution. The proteins and/or are then extracted from the combined cell samples by ultra-centrifugation, or other known techniques well known in the art. For example, antibodies may be used to immunoprecipitate certain proteins, complexes of proteins, as well. The particular method used may be dependent on the particular proteins of interest, as is known in the art. Lipids may be extracted out The mixture of proteins/lipids is then separated into individual proteins or lipids or small groups of proteins or lipids, also by known techniques, such as one- and/or two-dimensional electrophoresis, ultra-centrifugation, liquid chromatography or affinity binding. Two-dimensional sodium dodecylsulfate-polyacrylamide gel electrophoresis ("SOS-PAGE") may also be used, for proteins for example. If an individual protein or lipid is extracted from the combined cell samples, such as by use of an antibody, extraction techniques or other approaches, a separate separation step may not be necessary.

The proteins and lipids isolated may be further processed to provide peptides or cleaved lipids. In the case of separated proteins, these are preferably digested into peptides. Preferably, the proteins are digested by a proteolytic enzyme. Trypsin is preferred because it cleaves precisely at the sites of lysine and arginine, yielding doubly-charged peptides which typically have a length of from about 5 to 50 amino acids and a molecular weight of between about 700-5,000. Such peptides are particularly appropriate for analysis by mass spectroscopy, especially by electrospray ionization mass spectroscopy. Other site specific proteolytic enzymes which may be used include Ly-C, Asp-N and Glu-C, for example. Pepsin, subtilisin and proteinase 1 c are low specificity enzymes which may also be used. Chemical reagents may also be used to digest the proteins or lipids. For example, cyanogen bromide may be used to cut a protein into peptides at the site of methionine. BNPS-skatole may be used to cleave at the site of tryptophan. Acid hydrolysis may also be used. The proteins, peptides and lipids may also be processed by separating the proteins, peptides and lipids and then cleaving glycans therefore using methods well known in the art (e.g., PNGaseF treatment and β-elimination for N- and O-linked glycans, respectively). Glycans may be further separated using standard separation techniques including liquid chromatography (e.g., reverse phase HPLC).

The proteins, digested proteins, lipids or processed lipids, each of which contains glycan, are then subjected to mass spectroscopy. Any mass spectrometer may be used to analyze the peptides or proteins. For example, the mass spectrometer may be a Matrix-Assisted Laser Desorption/Ionization ("MALDI") Time-of-Flight ("TOF") Mass Spectrometer, available from PerSeptive Biosystems, Framingham, Mass.; an Electrospray Ionization ("ESI") ion trap mass spectrometer, available from Finnigan MAT, San Jose, Calif.; or an ESI quadrupole mass spectrometer, available from Finnigan MAT or the Perkin-Elmer Corporation, Foster City, Calif. A linear ion trap mass spectrometer (LTQ, ThermoFisher) or a hybrid linear ion trap Fourier transform ion cyclotron resonance mass spectrometer (LTQ-FT, ThermoFisher) may also be used.

A simple mixture of from 1 to about 5 digested proteins, lipids or glycans can be analyzed by single-stage mass spectroscopy with any of the mass spectrometers discussed above. Mixtures of greater than six digested proteins are preferably analyzed by a two-stage tandem mass spectroscopy procedure involving collision produced dissociation ("CID"), as is known in the art.

While preferred, the digestion of proteins is not required. One or several whole proteins containing glycan can also be subjected to mass spectroscopy, avoiding the need for digesting the proteins into peptides, as is known in the art. Single-stage mass spectroscopy may be used to analyze mixtures of large numbers of whole proteins containing glycans simultaneously.

The glycans, lipids, proteins or peptides subjected to the mass spectroscopy are also preferably identified. The identification step can take place at any time after separation or extraction of a single protein, peptide, lipid or glycan. Protein, peptide, lipid and glycan identification software which uses algorithms to compare the mass spectrum with a database of proteins, peptides, lipids and glycans are available. One such algorithm, ProFound, uses a Bayesian algorithm to search protein or DNA databases to identify the optimum match between the experimental data and the protein in the database. ProFound may be accessed at prowl.rockefeller.edu and proteometrics.com. Profound accesses the non-redundant database (NR). Alternative algorithms for protein identification include: Mass Search cbrg.inf.ethz.ch/subsection 3.sub.-3.html); MOWSE www.seqnet.dl.ac.uk//mows.html); MSFIT prospector.ucsf.edu/ucsfhtml/msfit.htm); Peptide Mass Search www.mdc-berlin.de/.about.emu/peptide_mass.html); and Peptide Search www.mann.embl_heidelberg.de/services/peptide search/fr_peptide searchform.html). See also, James, Peter, "Protein identification in the post-genome era: the rapid rise of proteomics", Q. Rev. Biophysics, Vol. 30, No. 4, pp. 279-331 (1997). Lipids may be identified from mass spectrometry data (especially tandem mass spectrometry) using, inter alia, Lipid Qualitative/Quantitative Analysis (LipidQA) software platform and related software See, for example Song, et al., *Journal of the American Society for Mass Spectrometry*, October 2007, Pages 1848-1858; Yetukuri, et al., *BMC Syst Biol.* 2007; 1: 12., Published online 2007 Feb. 15.

The proteins, peptides and lipids can also be identified by electrophoresis, antibodies Edman sequencing, bioassay, lipid extraction, liquid chromatography (reverse phase HPLC) and analysis, NMR or by other methods well known and used in the art, after separation. Glycans may be identified by liquid chromatography (HPLC), NMR and mass spectrometry as otherwise discussed herein.

The ratios of the peak intensities of each pair of peaks are then computed. The ratios give a measure of the relative amount of glycan in each sample, as discussed further, below. The peak intensities are calculated in a conventional manner.

Total content of glycans is determined and/or structural determination of glycan structures is then made using standard methods available in the art (e.g. fragmentation rules and glycoworkbench (see dkfz-heidelberg.de/spec/EURO-CarbDB/GlycoWorkbench/ as well as NMR analysis).

Because of the difference between the masses of the glycans from control samples grown in light glutamine and modulated samples grown in heavy glutamine, the results of the mass spectroscopy will generally be a plurality of pairs of closely spaced peaks, each peak being at a slightly different m/z ratio (+1, +2, etc. depending the number of aminosugars on a glycan group). Since the enriched isotope is typically heavier than the most abundant naturally occurring isotope ($^{15}$N versus $^{14}$N, for example), the peak at the higher m/z ratio is generally indicative of the relative abundance of the glycan from a labeled glycan grown in the medium enriched with heavy glutamine. The peak at the lower m/z ratio is generally indicative of the relative abundance of the glycan from a non-labeled glycan grown in medium containing light glutamine.

Since the number of cells in the modulated sample may differ from the number of cells in the control sample, for any given pair of peaks, the intensity of a peak corresponding to a glycan from the modulated sample may differ from the intensity of the peak corresponding to the same glycan from the control sample. The ratios between many of the pairs of peaks (which are indicative of protein, peptide and lipid fragments and not labeled glycans), will generally be the same. A deviation from the regularly-observed ratio indicates a difference in the relative quantity of a glycan, between the two cell samples which may be caused by the modulation to which one of the cell samples has been subjected. The difference can be quantified in accordance with the present invention.

In preferred methods according to the present invention, the control sample and modulated sample are combined before processing and analysis. Because the cell samples are combined, other sources of differences in the intensities of the peaks, such as variations in the extraction efficiency of a particular protein or lipid from cell sample, the subsequent extraction efficiency of a protein or lipid from the gel or other absorption media, the digestion efficiency of the enzyme used (if any), the ionization efficiency of the mass spectrometer for a particular protein, peptide, lipid or glycan and other such factors, affect both cell pools equally. These factors should not, therefore, affect the observed ratios. Analyzing the ratio of the pair of peaks compensates for differences in mass intensities resulting from differences in the ionization efficiency of the mass spectrometer for a particular glycan. Isotopically labeling one of the two cell samples and observing the ratio between the peaks of the isotopically labeled and non-isotopically labeled glycans also compensates for differential effects between the cell samples themselves, such as the presence of a different number of cells in each, providing an internal normalization between the cell samples. The method of the invention can also be extended to comparing the effects of two or more modulations by preparing three or more cell samples and analyzing the samples accordingly, preferably in each case combining a modulated sample with a control sample and then processes and analyzing the samples for overall glycan content, specific glycan content and structural information related to the existence of glycans in the sample.

The present invention therefore provides a simple-to-implement but powerful isotopic labeling strategy for glycans in cell culture systems. The present invention relies on the fact that the amide side chain of Gln is the sole nitrogen donor for UDP-GlcNAc via the hexosamine biosynthetic pathway and that UDP-GlcNAc is the substrate for the biosynthesis of UDP-GalNAc and CMP-Neu5Ac(Gc). Thus, the present inventors demonstrate here, using mouse ES cells, that replacement of the normal Gln supplement with amide-$^{15}$N-Gln allows for nearly complete isotope labeling of GlcNAc, GalNAc, and NeuAc residues of N-linked and O-linked glycans with a 72 hour labeling strategy.

EXPERIMENTAL PROCEDURES

Cell Culture

Murine embryonic stem cells (ES) were cultured essentially as previously described [24]. The ES cell culture media was composed of Dulbecco's modified Eagle's medium (DMEM) supplemented with 10% fetal calf serum (FCS, Commonwealth Serum Laboratories), 2 mM L-glutamine (either $^{14}$N or amide-$^{15}$N), 0.1 mM 2-mercaptoethanol, and 1000 U/ml recombinant murine leukemia inhibitory factor (LIF) (ESGRO, Chemicon International). Amide-$^{15}$N-Gln (98% purity) was purchased from Cambridge Isotopes Inc (Andover, Mass.). The ES cells were cultured at 37° C. under 10% $CO_2$. The media was changed daily for 3 days, after which the ESCs ($1\times10^7$) were collected by dissociation buffer and scraping, placed into a 15 ml conical tube, and pelleted at 1,000 g. The cells were washed 3 times in ice cold phosphate buffered saline (PBS) followed by centrifugation at 1000 g after each wash. All supernatant was removed from the tube and the cell pellets were stored at −80° C. until analysis.

ES Cell Lysis, Delipidation, Glycan Release, and Permethylation

The isolation of permethylated N- and O-linked permethylated glycans was essentially as previously described[14, 22, 23, 25]. Briefly, cells were resuspended in water and lysed by sonication. Delipidation was carried out using organic extraction in chloroform:methanol:water. The resulting proteins were subjected to trypsin digestion and glycans were released by PNGaseF treatment and β-elimination for N- and O-linked glycans, respectively. Reverse-phase enriched glycans were permethylated with methyl iodide and purified again by reverse-phase enrichment and dried down.

MS Analysis of the Permethylated Glycans

The glycans were analyzed as previously described[14, 22, 23, 25] on either a linear ion trap mass spectrometer (LTQ, ThermoFisher) or on a hybrid linear ion trap Fourier transform ion cyclotron resonance mass spectrometer (LTQ-FT, ThermoFisher). Briefly, permethylated glycans were dissolved in a total of 50 µL of sample: 15 µL of 100% methanol followed by the addition of 35 µL of 1 mM NaOH in 50% methanol and infused directly into the mass spectrometer using a nanospray ion source with a fused-silica emitter (360×75×30 µm, SilicaTip™, New Objective) at 2.0 kV capillary voltage, 200° C. capillary temperature, and a syringe flow rate of 0.4 µL/min. Full ITMS (Ion trap mass spectrometry) spectra in positive ion and profile mode were collected at 400-2000 m/z for 30 sec with 5 microscans and 150 maximum injection time (ms). The centroid MS/MS spectra following collision-induced dissociation (CID) were obtained from 400 to 2000 m/z at 34% and 28% normalized collision energy for N- and O-linked glycans respectively, 0.25 activation Q, and 30.0 ms activation time by total ion mapping (TIM). Parent mass step size and isolation width were set at 2.0 m/z and 2.8 m/z respectively for automated MS/MS spectra with TIM scans. MS" experiments were manually carried out in profile mode. Glycan precursor ions were isolated for MS" using an isolation width of 2.5 m/z. For FTICR analysis, an isolation width of 10 m/z at 100,000 resolution was used. Manual interpretation of all glycan structures was carried out relying on fragmentation rules and glycoworkbench (at website dkfz-heidelberg.de/spec/EUROCarbDB/GlycoWorkbench/).

Results

Mechanism for Isotope Incorporation into Glycoconjugates

Figure 1B:
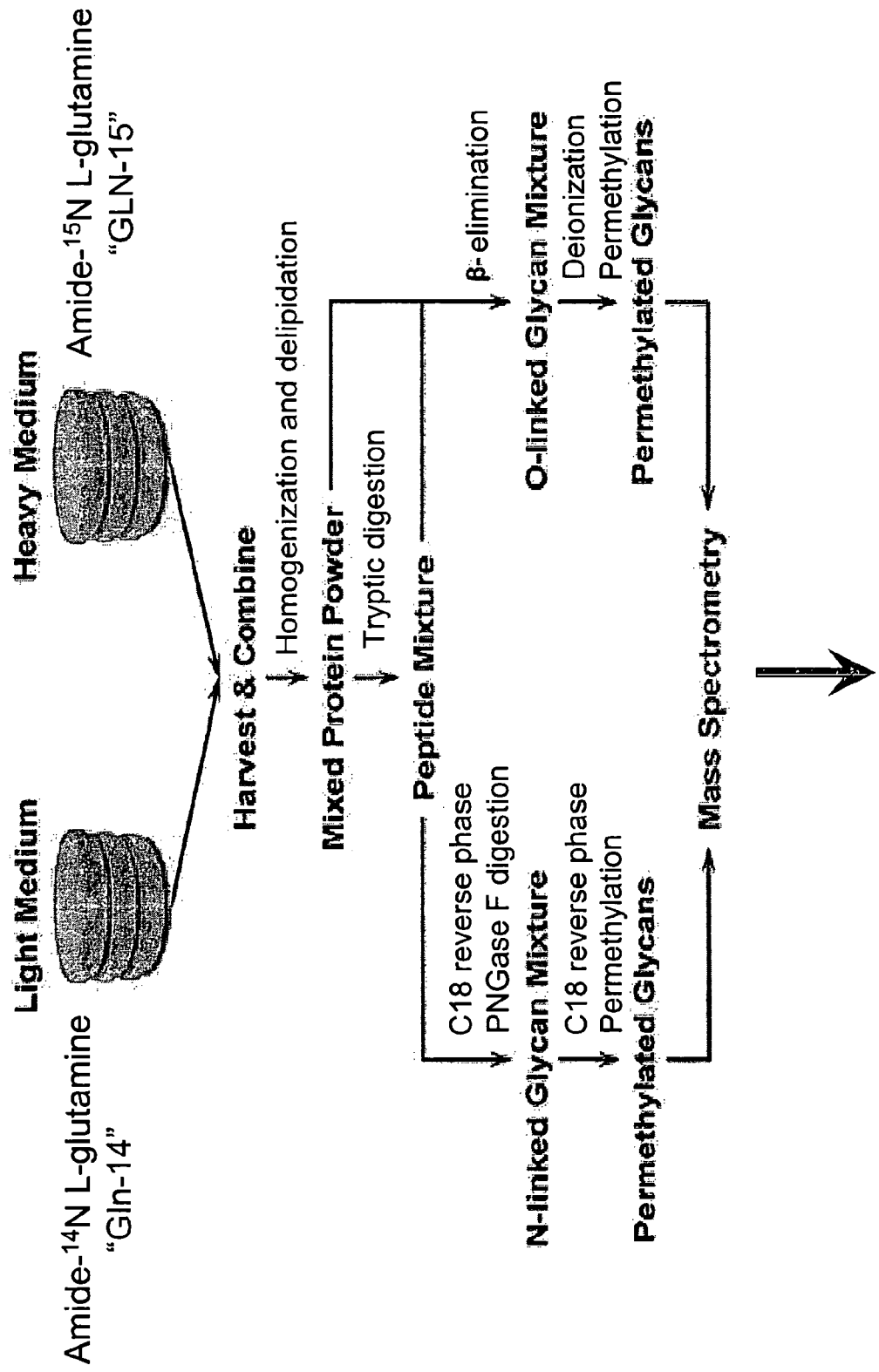
FIG. 1B shows a flow chart of the isolation and analysis steps used to label murine ES cells with or without heavy Gln and then isolated both N- and O-linked glycans from proteins for mass spectrometry analysis.
Figure 1B:
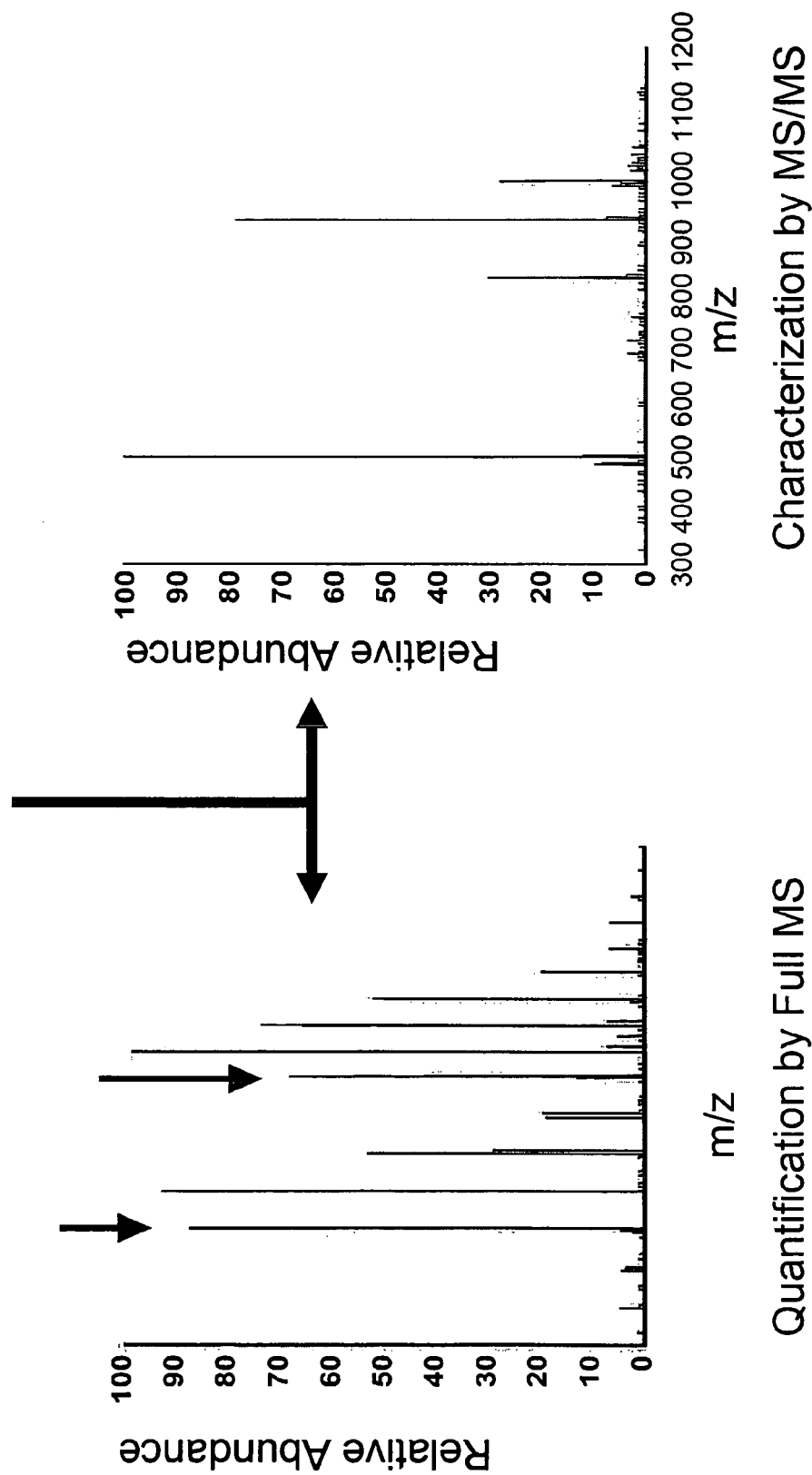

The hexosamine biosynthetic pathway converts the glycolysis intermediate fructose-6-phosphate into UDP-GlcNAc ([26], FIG. 1A). The first and rate-limiting step in this pathway converts fructose-6-phosphate to glucosamine-6-phosphate with the concomitant conversion of Gln to Glu[27]. Thus, the side-chain amide of Gln is the source of nitrogen in the production of UDP-GlcNAc. The other major aminosugar-containing sugar nucleotides, UDP-GalNAc and CMP-sialic acid, are biosynthesized from UDP-GlcNAc[28, 29]. Thus, theoretically all GlcNAc, GalNAc, and sialic acid containing molecules can be isotopically labeled via amide-$^{15}$N-Gln supplementation into the cell culture media (FIG. 1).

Initial experiments were performed to evaluate the possibility of using metabolic labeling as a method to incorporate a stable isotope into the glycans of cells grown in culture. In these experiments, R1 murine embryonic stem cells (mESCs) were grown using standard conditions. The media used for cell culturing is typically supplied without glutamine, as this amino acid decomposes to glutamic acid and ammonia under aqueous conditions. This simplifies the IDAWG labeling approach as there is no need to specifically deplete the media of Gln. Amide-$^{15}$N-Gln is used instead of the $^{14}$N-version to supplement the media at the recommended concentration, which in this case was 2 mM. This straightforward substitution is the only alteration to the normal cell culturing procedure needed for IDAWG. Thus, the present inventors labeled murine ES cells for three days with or without heavy Gln and then isolated both N- and O-linked glycans from proteins for mass spectrometry-based analysis (FIG. 1B).

$^{15}$N Incorporation into N-Linked Glycans

Figure 2:
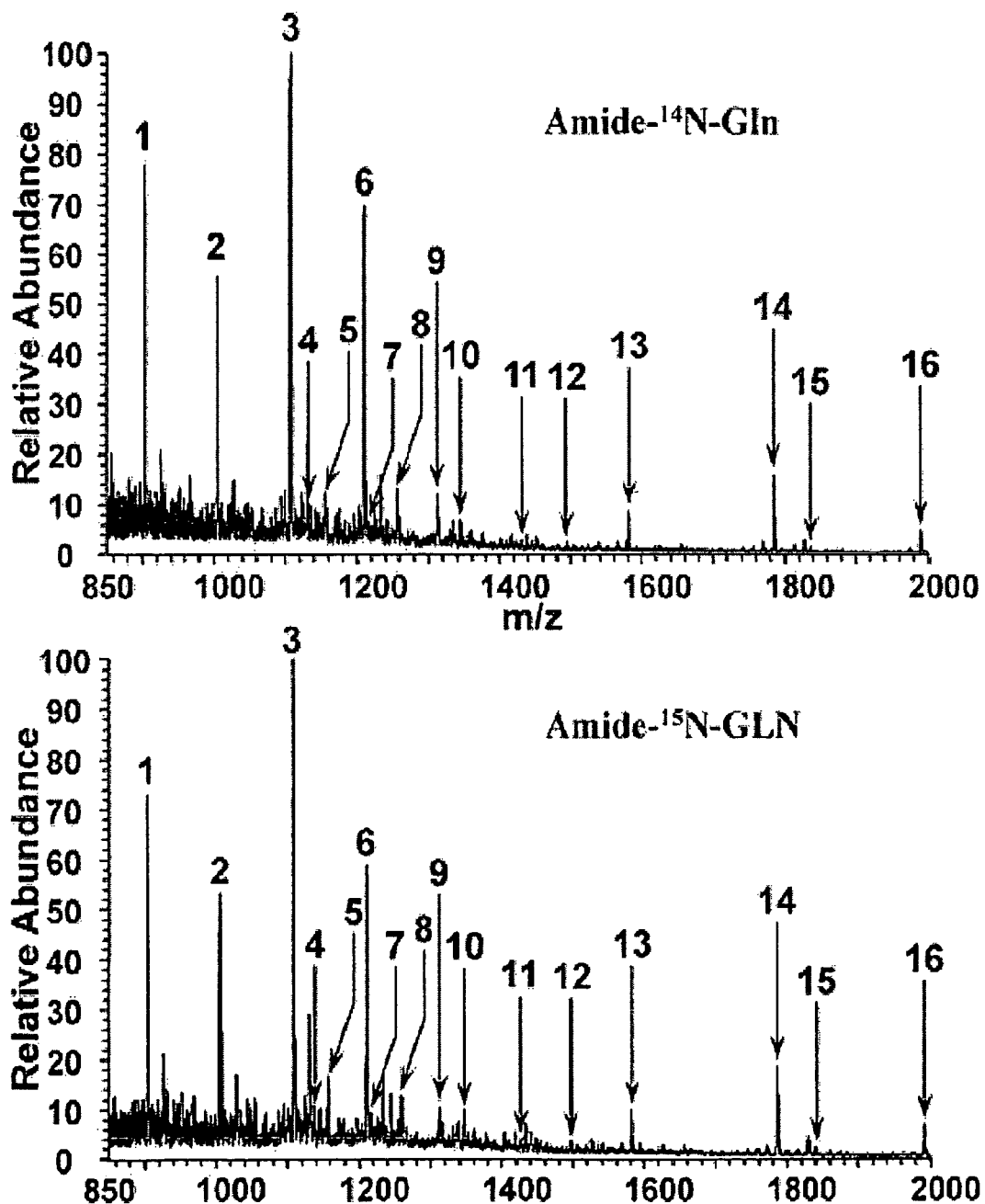
FIG. 2 shows the full spectra of permethylated N-linked glycans released from mESCs grown in either $^{14}$Gln or $^{15}$NGln.
Figure 3:
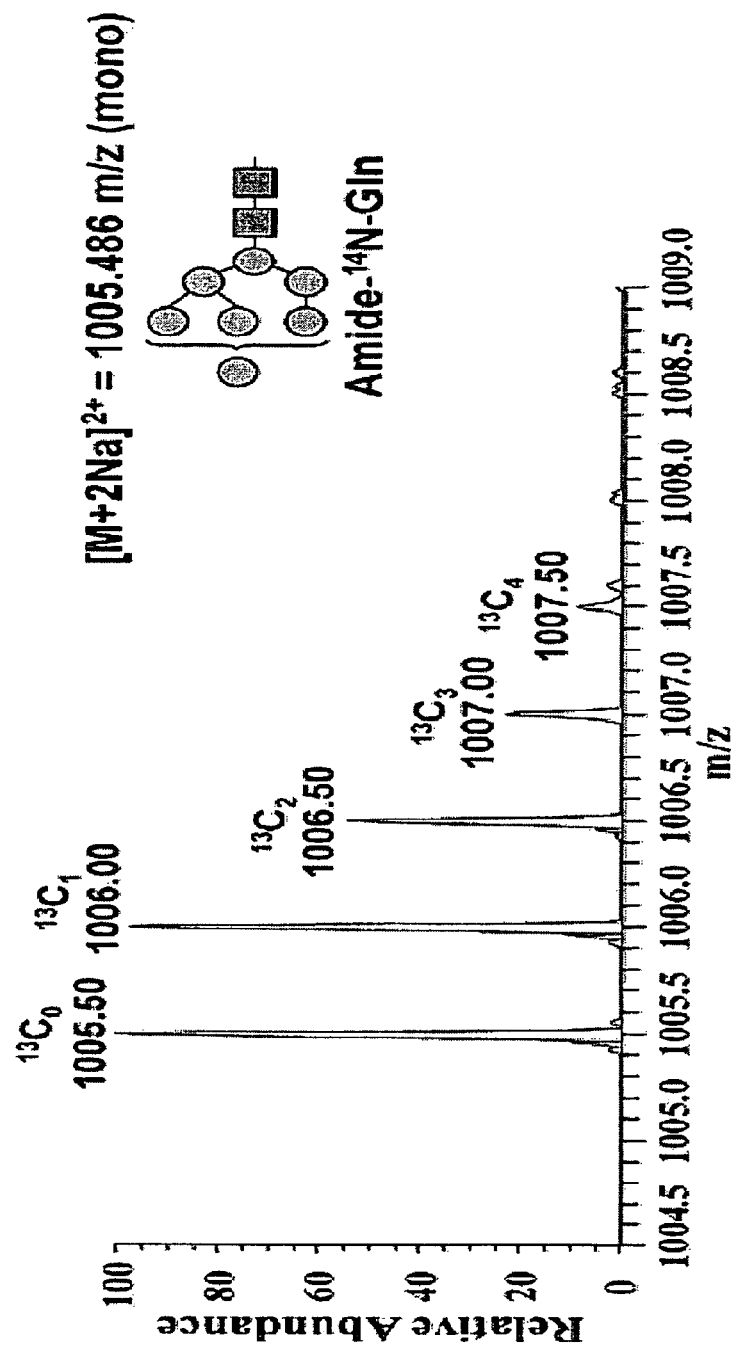
FIG. 3 shows a closer inspection of the doubly charged molecular ion, (M+2Na)$^{2+}$, resulting from the GlcNAcsMan$_7$ glycan, which appears at 1005.5 and 1006.5 m/z units from glycans grown in the $^{14}$N and $^{15}$NGln media.
Figure 3:
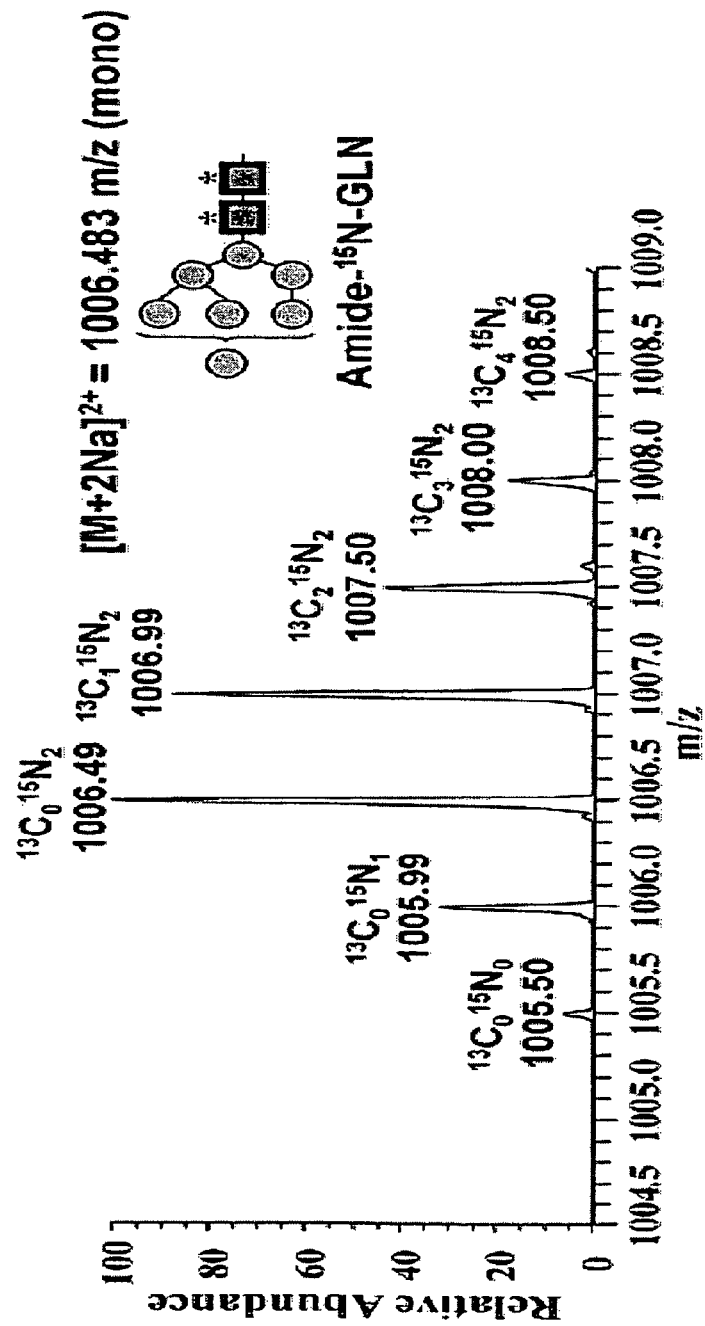
Figure 4A:
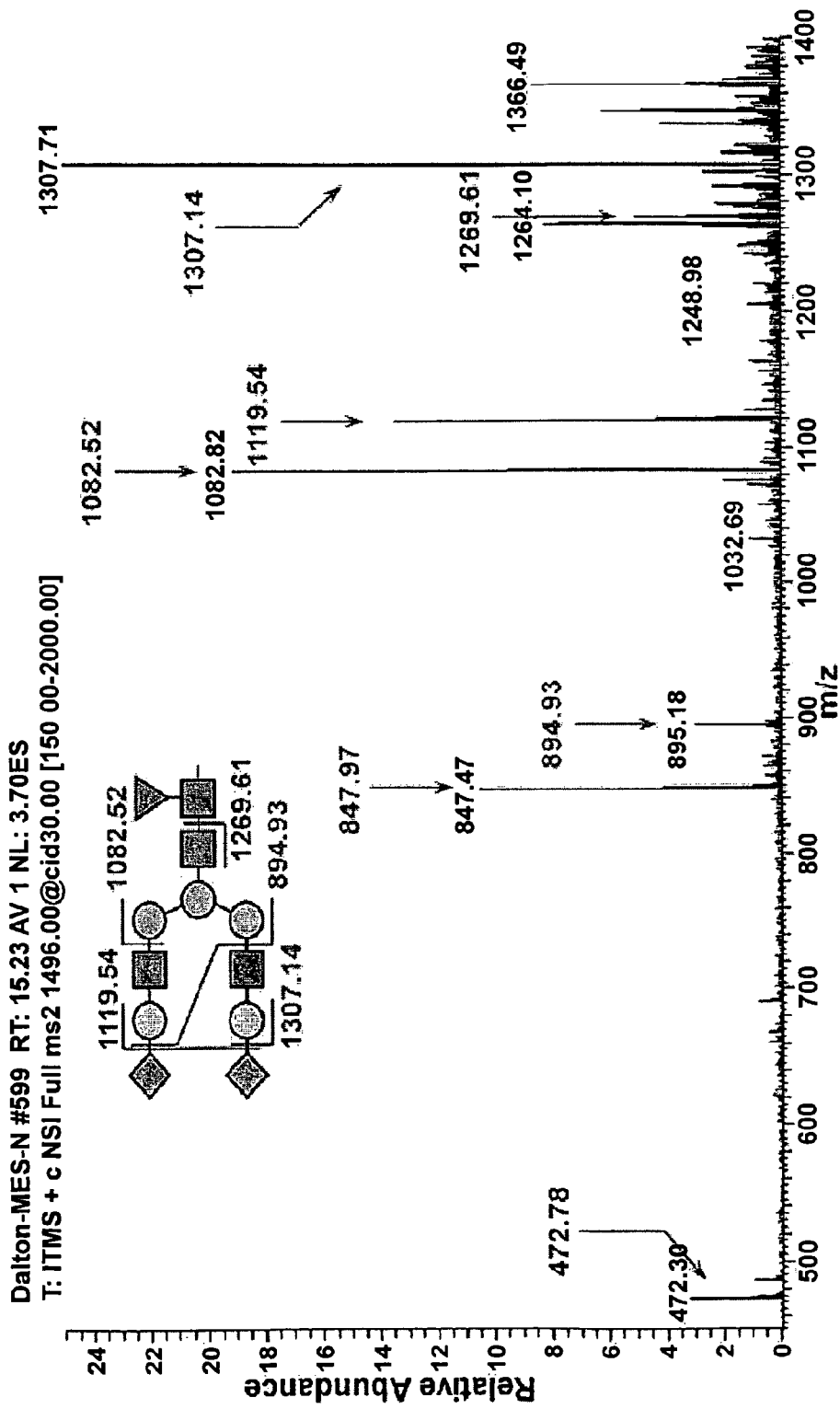
FIGS. 4A and 4B show that fragmentation of both a heavy and a light labeled core fucosylated, fully sialyated, biantennary N-linked glycan display fragments consistent with $^{15}$N-incorporation into Neu5Ac as well as core and antennary GlcNAc residues.
Figure 4B:
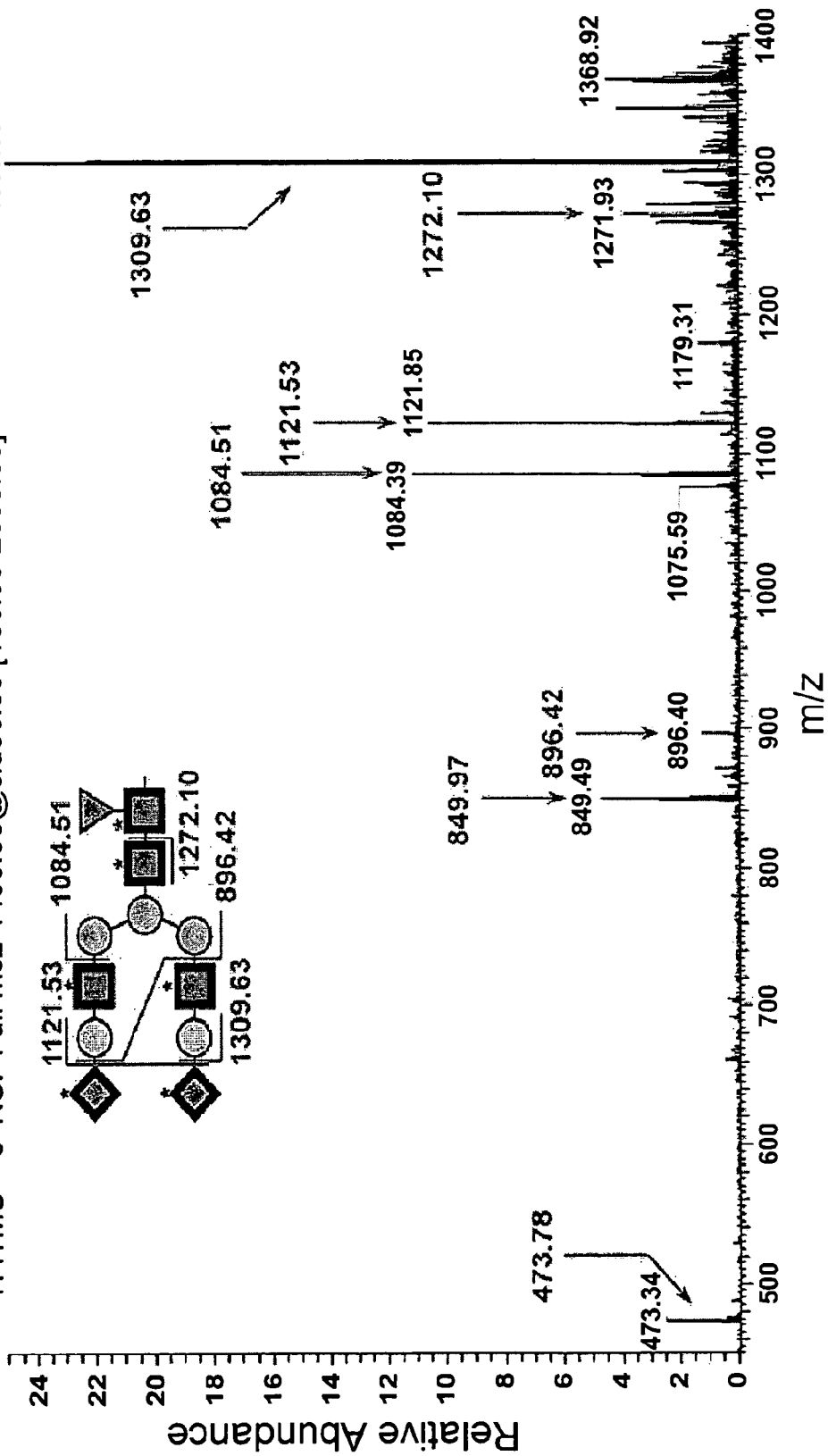
Figure 5A:
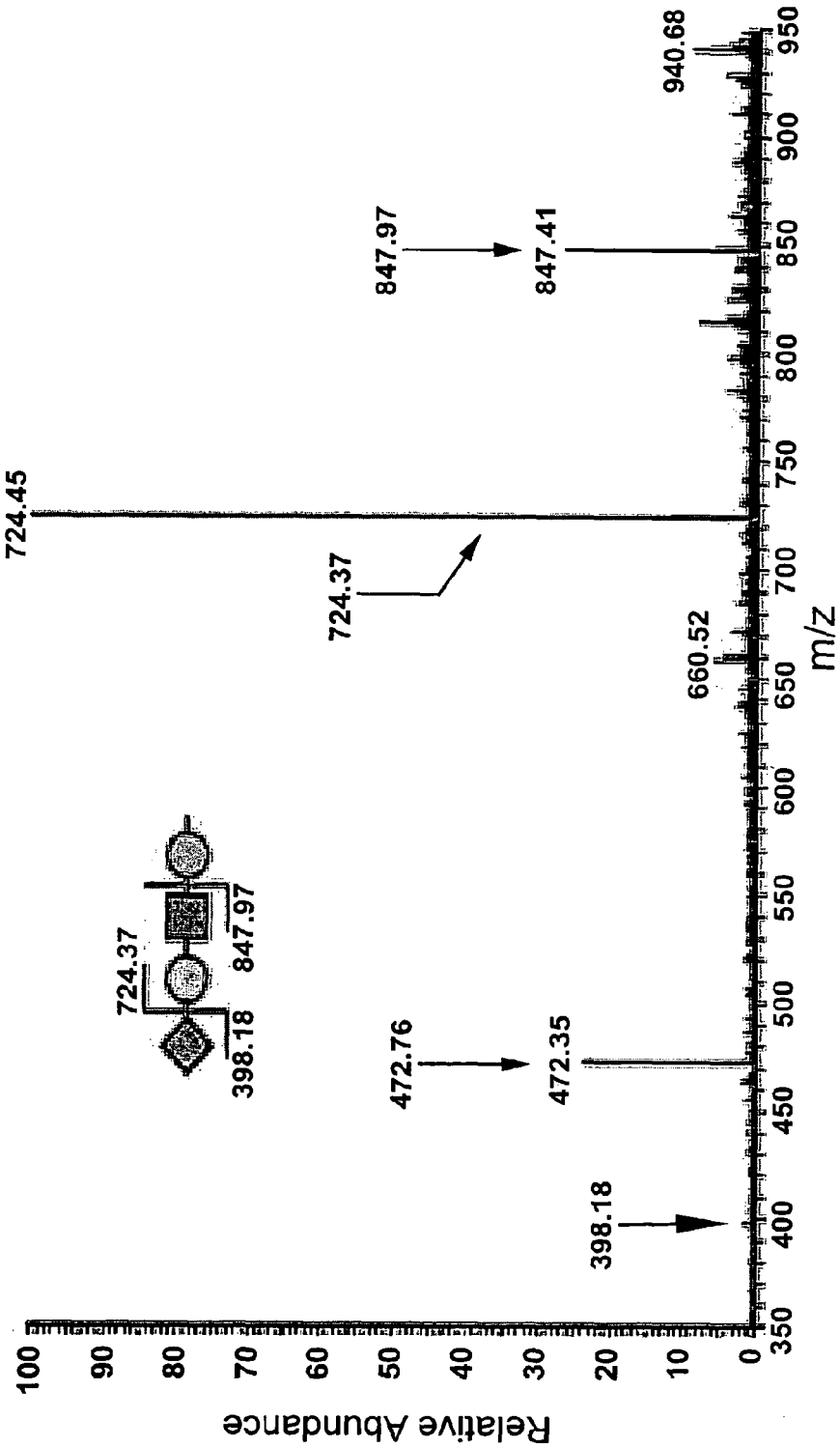
FIGS. 5A-F are illustrative of the incorporation of $^{15}$N into all aminosugars contained in O-glycans, both MS/MS spectra from heavy and light isolated samples following fragmentation are shown for an O-Man initiated glycan containing GlcNAc and Neu5Ac, an O-GalNAc initiated structure containing a GlcNAc and an O-GalNAc initiated structure containing two Neu5Ac residues.
Figure 5B:
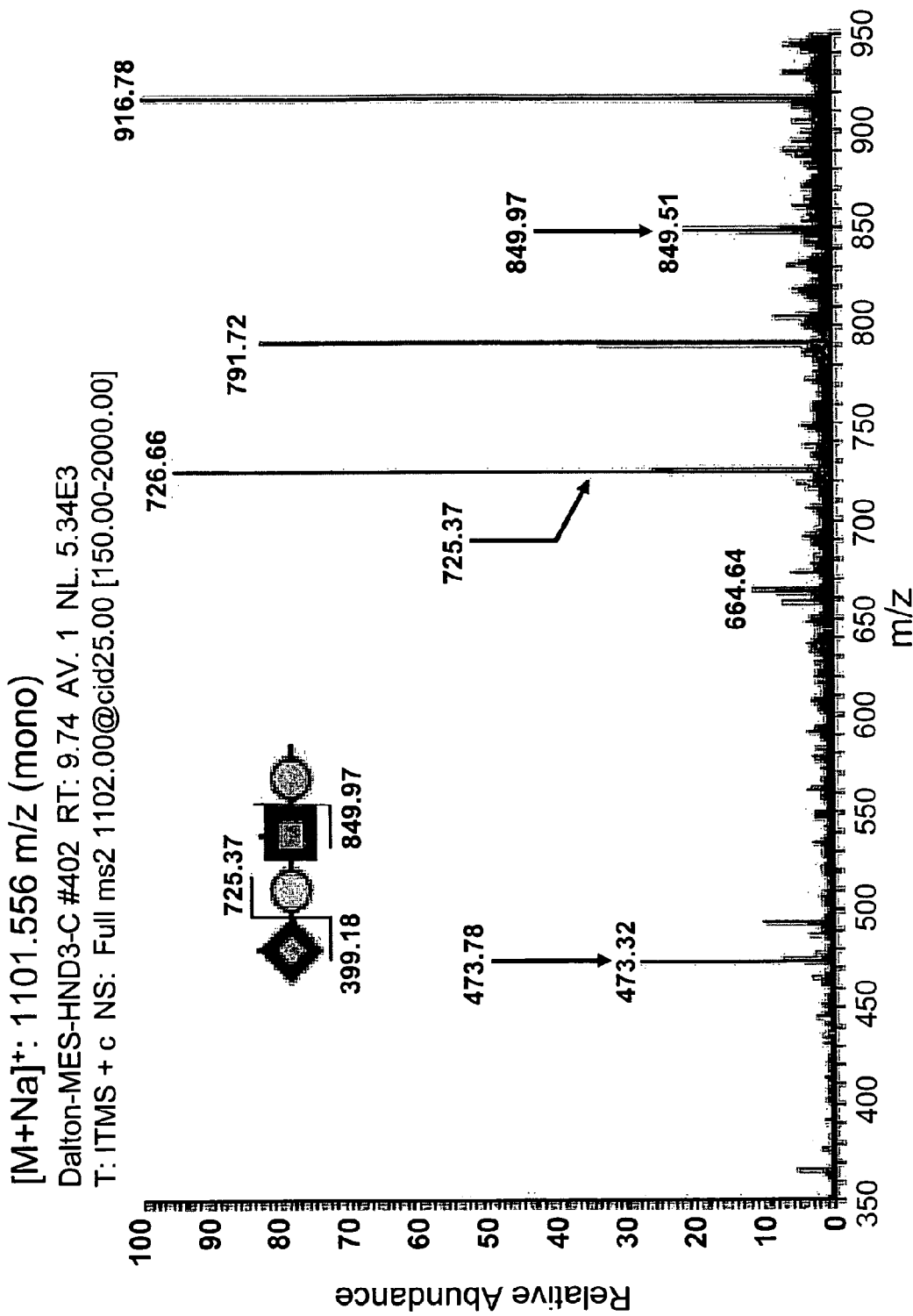
Figure 5C:
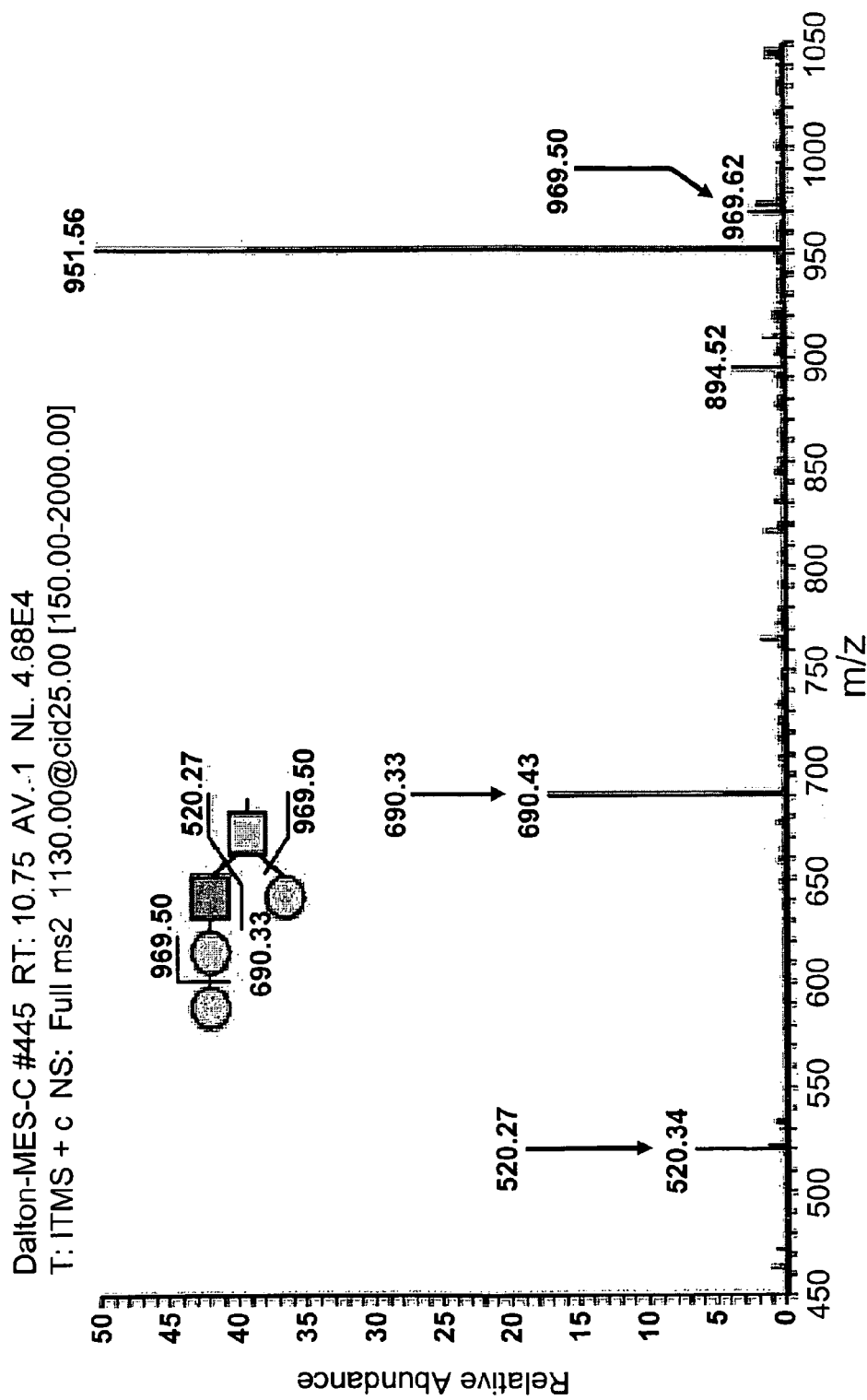
Figure 5D:
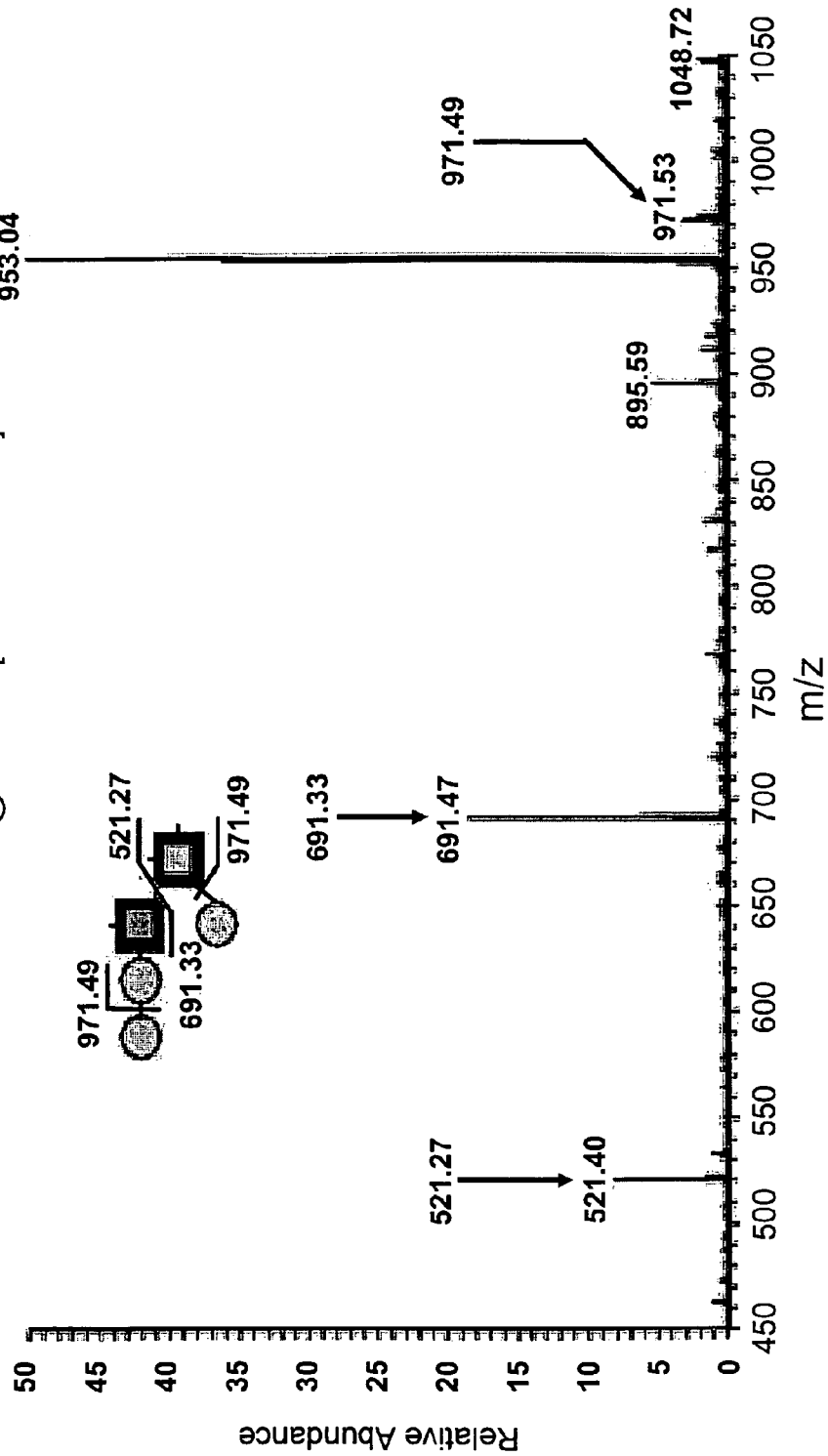
Figure 5E:
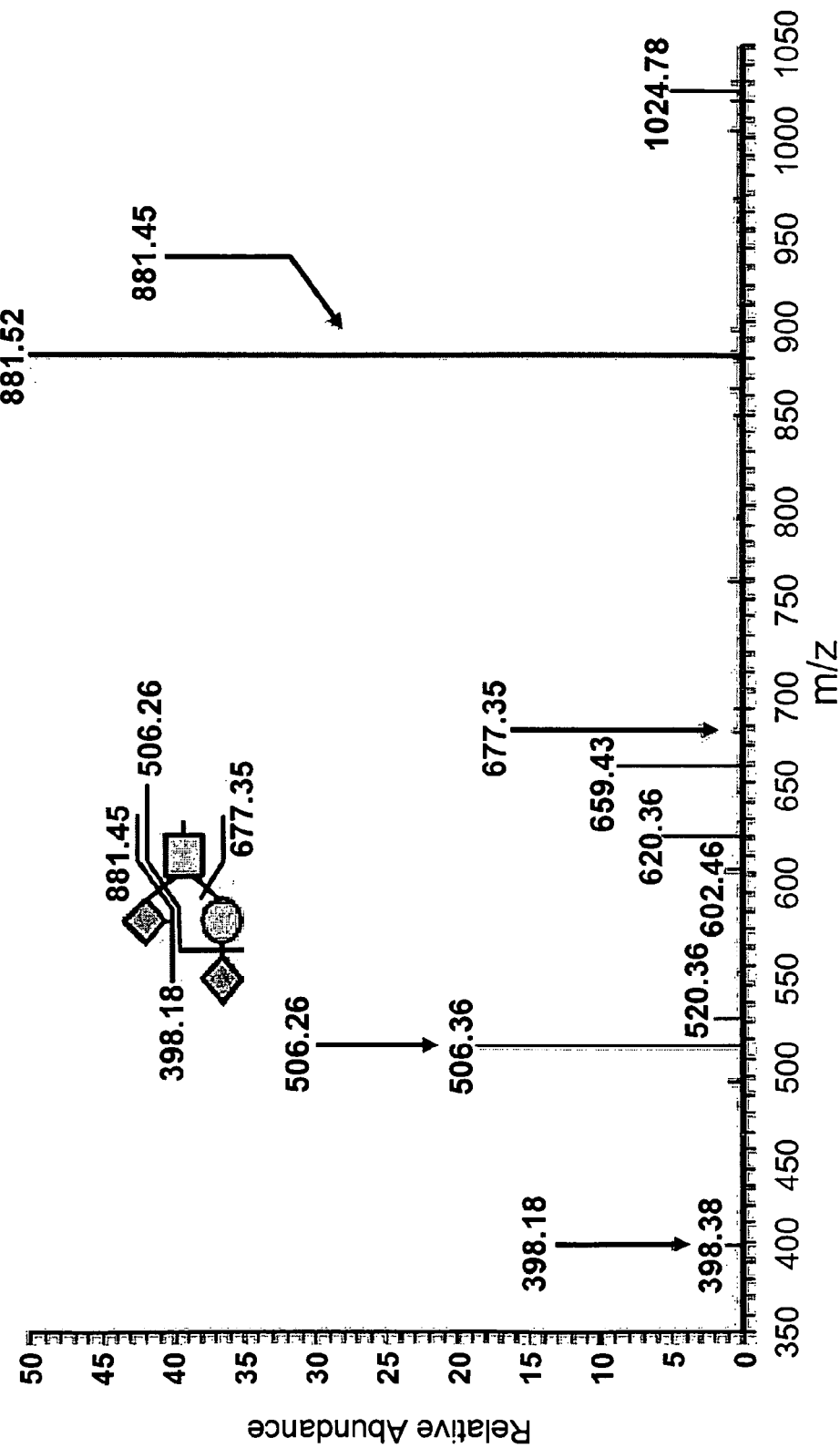
Figure 5F:
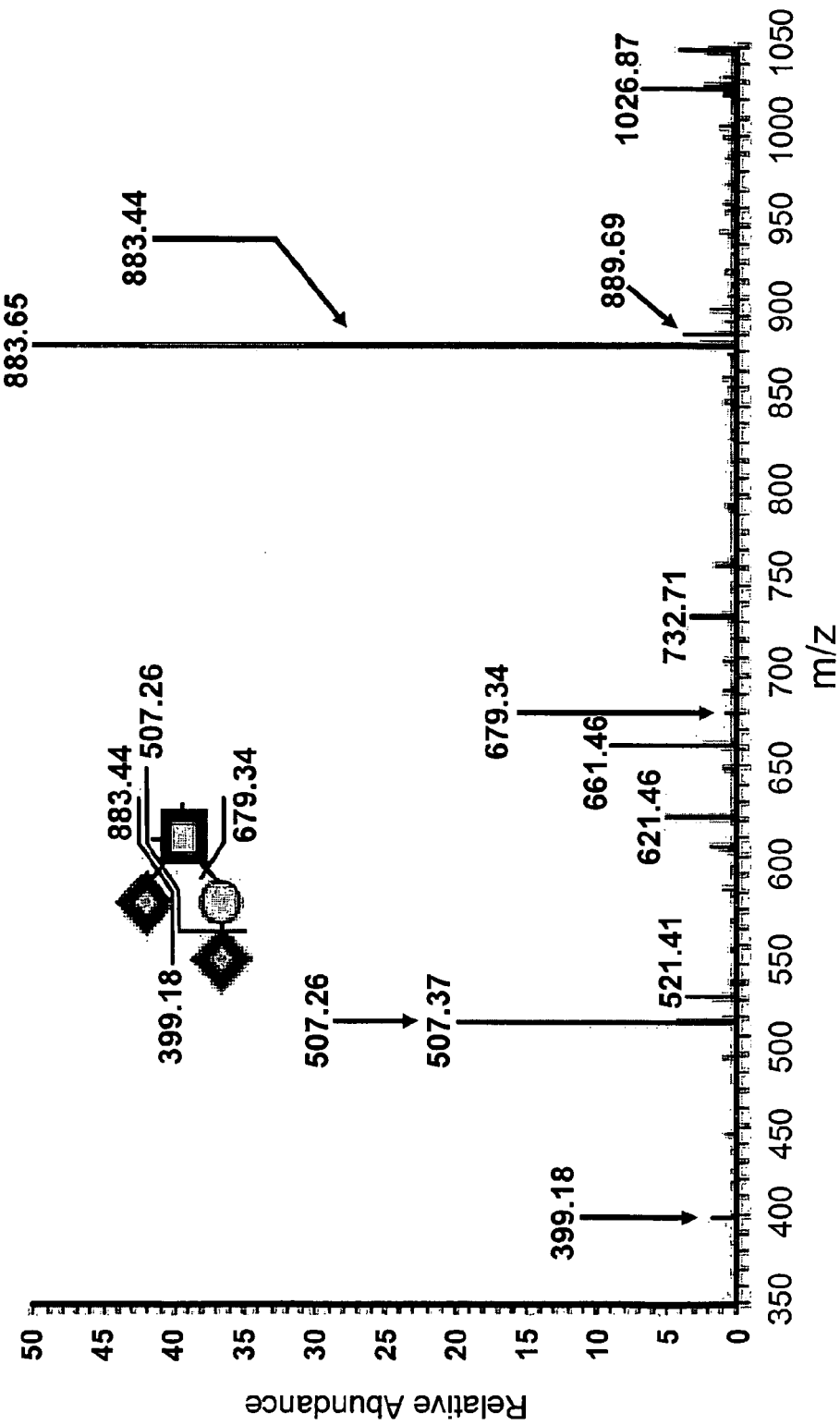

The incorporation of $^{15}$N into the N-linked glycans of mESCs was investigated by comparing the full spectra of the permethylated N-linked glycans released from cells grown in either $^{14}$N-Gln or amide-$^{15}$N-Gln (FIG. 2). Both samples were subjected to total ion mapping analysis and MS$^n$ when necessary to confirm the structures (data not shown). The abundant ions observed in these spectra are predominantly high mannose glycans (GlcNAc$_2$Man$_{5-9}$) that are either singly or doubly charged (structures 1-3, 6, 13-14, and 16 from FIG. 2). Comparison of these two spectra reveals that the high mannose glycan ions obtained from the cells grown in the amide-$^{15}$N-Gln containing media are increased by 1 m/z unit for the doubly charged ions and 2 m/z units for the singly charged ions. This is the expected result provided that $^{15}$N has been incorporated into the two core GlcNAcs contained in these glycans, which are the only nitrogens present in high mannose glycans. Also contained within the full spectra are ions representing complex glycans containing GlcNAc (structures 4, 5, 7, 8, 10, 11, 12, an 15 from FIG. 2) and Neu5Ac (structure 12 from FIG. 2) residues that are seen to be shifted in the amide-$^{15}$N-Gln samples by the appropriate mass for $^{15}$N-incorporation into GlcNAc and Neu5Ac. For calculation of labeling efficiencies, the samples were analyzed on a hybrid LTQ-FT instrument. Closer inspection of the doubly charged molecular ion, $(M+2Na)^{2+}$, resulting from the GlcNAc$_2$Man$_7$ glycan, which appears at 1005.5 and 1006.5 m/z units from glycans grown in the $^{14}$N and 1-$^{15}$N Gln media, respectively, is shown in FIG. 3. In these spectra, the most intense ion appears at the monoisotopic mass calculated with either $^{14}$N or two $^{15}$N, demonstrating that the majority of this glycan has $^{15}$N incorporated into both possible sites. Ions are present that correspond to under labeling, i.e., the incorporation of zero and one $^{15}$N, however the dominant species is fully labeled. Zoom scans were performed on several structures containing theoretically 2-5 $^{15}$N-residues. Calculations performed on the ratios of the intensities of the different isotopes in the $^{15}$N spectrum indicate an average 96.2% incorporation of $^{15}$N into N-linked glycans (Table 1, FIG. 6), which is very similar to the extent of $^{15}$N in the glutamine used for this experiment (98%). Thus, $^{15}$N from amide-$^{15}$N-Gln becomes extensively incorporated into amino sugars of N-linked glycans. Furthermore, MS/MS spectra resulting from the fragmentation of N-linked glycans display a pattern consistent with the labeling. For example, fragmentation of both a heavy and a light labeled core fucosylated, fully sialyated, biantennary N-linked glycan display fragments consistent with 15N-incorporation into Neu5Ac as well as core and antennary GlcNAc residues (FIG. 4). This labeling may greatly aid in the assignment of structures based on fragmentation and provides the possibility of performing quantification based on multiple peaks in the MS/MS spectra.

$^{15}$N Incorporation into O-linked Glycans

To study the incorporation of $^{15}$N into the O-linked glycans of mESCs, the full spectra of the permethylated O-linked glycans released from cells grown in either $^{14}$N-Gln or amide-$^{15}$N-Gln were compared. Both samples were subjected to total ion mapping analysis and MS$^n$ when necessary to confirm the structures. To illustrate the incorporation of $^{15}$N into all 3 aminosugars contained in O-glycans, both MS/MS spectra from heavy and light isolated samples following fragmentation are shown for an O-Man initiated glycan containing GlcNAc and Neu5Ac, an O-GalNAc initiated structure containing a GlcNAc, and an O-GalNAc initiated structure containing two Neu5Ac residues (FIG. 5). The isolation m/z and fragmentation profile of all 3 O-linked structures are consistent with $^{15}$N-incorporation into all GlcNAc, GalNAc, and NeuAc monosaccharides. As can be seen from the fragmentation patterns, the reducing end GalNAc is isotopically labeled in the heavy samples as are the GlcNAc and NeuAc in the extended chains. These results highlight that $^{15}$N is incorporated into all 3 aminosugars and that fragmentation of light and heavy structures should aid greatly in glycan assignment and quantification.

$^{15}$N Incorporation into Proteins

Shotgun proteomic experiments performed on peptides obtained from the $^{14}$N/$^{15}$N labeled samples identified peptides containing amide-$^{15}$N-Gln incorporated (data not shown). However, incorporation of $^{15}$N into other amino acids was not observed. This was the expected result as the first step in the conversion of Gln into other amino acids produces glutamic acid (Glu), which results in the loss of the amide-$^{15}$N. This is important as it simplifies database searching but leaves open the ability to perform relative quantification at the protein level as well using the Gln-containing peptides identified. In the event that isotopic labeling of both the peptides (beyond Gln-containing peptides) and the glycans is desired, the metabolic labeling approach described above could be combined with SILAC or another proteomic based isotopic labeling strategy.

The present technique provides for robust quantification of glycans released from proteins (data shown) and lipids (data not shown) between two samples. Furthermore, this technique provides a labeling strategy amenable for examining and quantifying glycopeptides directly. This strategy is demonstrated in examining the dynamic O-GlcNAc modification[30] on proteins isolated from light and heavy Gln-labeled cell culture systems. The observation that $^{15}$N-Gln also is incorporated into proteins, but no other heavy amino acids are observed as expected, provides a SILAC-like labeling strategy that may be used alone or in combination with heavy Arg/Lys SILAC[7] to theoretically quantify glycans, proteins, and glycoproteins/glycopeptides all from the same set of samples. Finally, the IDAWG strategy provides for the option of calculating the half-life of all aminosugar-containing glycans in a sample by completely labeling the sample first and then replacing the heavy Gln with light Gln and isolating and analyzing samples over a time-course. Accordingly, IDAWG forms a powerful new quantitative tool for exploring the biological role of glycans, glycoproteins, and glycolipids in cell culture systems.

REFERENCES

1. Liu, H.; Sadygov, R. G.; Yates, J. R., 3rd, A model for random sampling and estimation of relative protein abundance in shotgun proteomics. *Anal Chem* 2004, 76, (14), 4193-201.
2. Radulovic, D.; Jelveh, S.; Ryu, S.; Hamilton, T. G.; Foss, E.; Mao, Y.; Emili, A., Informatics platform for global proteomic profiling and biomarker discovery using liquid chromatography-tandem mass spectrometry. *Mol Cell Proteomics* 2004, 3, (10), 984-97.
3. Silva, J. C.; Denny, R.; Dorschel, C. A.; Gorenstein, M.; Kass, I. J.; Li, G. Z.; McKenna, T.; Nold, M. J.; Richardson, K.; Young, P.; Geromanos, S., Quantitative proteomic analysis by accurate mass retention time pairs. *Anal Chem* 2005, 77, (7), 2187-200.
4. Wang, W.; Zhou, H.; Lin, H.; Roy, S.; Shaler, T. A.; Hill, L. R.; Norton, S.; Kumar, P.; Anderle, M.; Becker, C. H., Quantification of proteins and metabolites by mass spectrometry without isotopic labeling or spiked standards. *Anal Chem* 2003, 75, (18), 4818-26.
5. Gygi, S. P.; Rist, B.; Gerber, S. A.; Turecek, F.; Gelb, M. H.; Aebersold, R., Quantitative analysis of complex protein mixtures using isotope-coded affinity tags. *Nat Biotechnol* 1999, 17, (10), 994-9.
6. Liu, P.; Regnier, F. E., An isotope coding strategy for proteomics involving both amine and carboxyl group labeling. *J Proteome Res* 2002, 1, (5), 443-50.
7. Ong, S. E.; Blagoev, B.; Kratchmarova, I.; Kristensen, D. B.; Steen, H.; Pandey, A.; Mann, M., Stable isotope labeling by amino acids in cell culture, SILAC, as a simple and accurate approach to expression proteomics. *Mol Cell Proteomics* 2002, 1, (5), 376-86.
8. Rao, K. C.; Carruth, R. T.; Miyagi, M., Proteolytic 18O labeling by peptidyl-Lys metalloendopeptidase for comparative proteomics. *J Proteome Res* 2005, 4, (2), 507-14.
9. Schnolzer, M.; Jedrzejewski, P.; Lehmann, W. D., Protease-catalyzed incorporation of 18O into peptide fragments and its application for protein sequencing by electrospray and matrix-assisted laser desorption/ionization mass spectrometry. *Electrophoresis* 1996, 17, (5), 945-53.
10. Vosseller, K.; Hansen, K. C.; Chalkley, R. J.; Trinidad, J. C.; Wells, L.; Hart, G. W.; Burlingame, A. L., Quantitative analysis of both protein expression and serine/threonine post-translational modifications through stable isotope labeling with dithiothreitol. *Proteomics* 2005, 5, (2), 388-98.
11. Wells, L.; Vosseller, K.; Cole, R. N.; Cronshaw, J. M.; Matunis, M. J.; Hart, G. W., Mapping sites of O-GlcNAc modification using affinity tags for serine and threonine post-translational modifications. *Mol Cell Proteomics* 2002, 1, (10), 791-804.
12. Yao, X.; Freas, A.; Ramirez, J.; Demirev, P. A.; Fenselau, C., Proteolytic 18O labeling for comparative proteomics: model studies with two serotypes of adenovirus. *Anal Chem* 2001, 73, (13), 2836-42.
13. Ong, S. E.; Foster, L. J.; Mann, M., Mass spectrometric-based approaches in quantitative proteomics. *Methods* 2003, 29, (2), 124-30.
14. Aoki, K.; Perlman, M.; Lim, J. M.; Cantu, R.; Wells, L.; Tiemeyer, M., Dynamic developmental elaboration of N-linked glycan complexity in the *Drosophila melanogaster* embryo. *J Biol Chem* 2007, 282, (12), 9127-42.
15. Bowman, M. J.; Zaia, J., Tags for the stable isotopic labeling of carbohydrates and quantitative analysis by mass spectrometry. *Anal Chem* 2007, 79, (15), 5777-84.
16. Hitchcock, A. M.; Costello, C. E.; Zaia, J., Glycoform quantification of chondroitin/dermatan sulfate using a liquid chromatography-tandem mass spectrometry platform. *Biochemistry* 2006, 45, (7), 2350-61.
17. Xia, B.; Kawar, Z. S.; Ju, T.; Alvarez, R. A.; Sachdev, G. P.; Cummings, R. D., Versatile fluorescent derivatization of glycans for glycomic analysis. *Nat Methods* 2005, 2, (11), 845-50.
18. Yuan, J.; Hashii, N.; Kawasaki, N.; Itoh, S.; Kawanishi, T.; Hayakawa, T., Isotope tag method for quantitative analysis of carbohydrates by liquid chromatography-mass spectrometry. *J Chromatogr A* 2005, 1067, (1-2), 145-52.
19. Xie, Y.; Liu, J.; Zhang, J.; Hedrick, J. L.; Lebrilla, C. B., Method for the comparative glycomic analyses of O-linked, mucin-type oligosaccharides. *Anal Chem* 2004, 76, (17), 5186-97.
20. Alvarez-Manilla, G.; Warren, N. L.; Abney, T.; Atwood, J., 3rd; Azadi, P.; York, W. S.; Pierce, M.; Orlando, R., Tools for glycomics: relative quantitation of glycans by isotopic permethylation using 13CH3I. *Glycobiology* 2007, 17, (7), 677-87.
21. Kang, P.; Mechref, Y.; Kyselova, Z.; Goetz, J. A.; Novotny, M. V., Comparative glycomic mapping through quantitative permethylation and stable-isotope labeling. *Anal Chem* 2007, 79, (16), 6064-73.
22. Atwood, J. A., 3rd; Cheng, L.; Alvarez-Manilla, G.; Warren, N. L.; York, W. S.; Orlando, R., Quantitation by isobaric labeling: applications to glycomics. *J Proteome Res* 2008, 7, (1), 367-74.
23. Bothelo, J. C.; Atwood, J. A., 3rd; Cheng, L.; Alvarez-Manilla, G.; York, W. S.; Orlando, R., QUIBL for the Comparative Glycomic Study of O-linked Glycans. *International Journal of Mass Spectrometry* 2008, IN PRESS.
24. Stead, E.; White, J.; Faast, R.; Conn, S.; Goldstone, S.; Rathjen, J.; Dhingra, U.; Rathjen, P.; Walker, D.; Dalton, S., Pluripotent cell division cycles are driven by ectopic Cdk2, cyclin A/E and E2F activities. *Oncogene* 2002, 21, (54), 8320-33.
25. Aoki, K.; Porterfield, M.; Lee, S. S.; Dong, B.; Nguyen, K.; McGlamry, K. H.; Tiemeyer, M., The diversity of O-linked glycans expressed during *Drosophila melanogaster* development reflects stage- and tissue-specific requirements for cell signaling. *J Biol Chem* 2008.
26. McClain, D. A., Hexosamines as mediators of nutrient sensing and regulation in diabetes. *J Diabetes Complications* 2002, 16, (1), 72-80.
27. Yki-Jarvinen, H.; Vogt, C.; Iozzo, P.; Pipek, R.; Daniels, M. C.; Virkamaki, A.; Makimattila, S.; Mandarino, L.; DeFronzo, R. A.; McClain, D.; Gottschalk, W. K., UDP-N-acetylglucosamine transferase and glutamine: fructose 6-phosphate amidotransferase activities in insulin-sensitive tissues. *Diabetologia* 1997, 40, (1), 76-81.
28. Kean, E. L.; Munster-Kuhnel, A. K.; Gerardy-Schahn, R., CMP-sialic acid synthetase of the nucleus. *Biochim Biophys Acta* 2004, 1673, (1-2), 56-65.
29. Thoden, J. B.; Wohlers, T. M.; Fridovich-Keil, J. L.; Holden, H. M., Human UDP-galactose 4-epimerase.

Accommodation of UDP-N-acetylglucosamine within the active site. *J Biol Chem* 2001, 276, (18), 15131-6.

30. Wells, L.; Vosseller, K.; Hart, G. W., Glycosylation of nucleocytoplasmic proteins signal transduction and O-GlcNAc. *Science* 2001, 291, (5512), 2376-8.

The invention claimed is:

1. A method for comparing the relative abundance of one or more glycans of interest in a modulated biological sample compared to a control sample comprising:
    culturing a first biological sample to be modulated in a first culture medium further comprising $^{15}$N-glutamine;
    culturing a control sample in a second culture medium identical to said first culture medium further comprising $^{14}$N-glutamine;
    modulating said first sample during culturing;
    processing said first sample and said control sample to extract proteins and/or lipids therefrom;
    separating said proteins and/or lipids from said samples after said processing step;
    optionally digesting said proteins into a plurality of peptides;
    optionally releasing glycans from said proteins, peptides and/or lipids and separating said released glycans from said proteins, peptides and/or lipids;
    subjecting said proteins, said peptides, said lipids and/or said optionally released glycans to mass spectroscopy to develop a mass spectrum; and
    determining the relative abundance of said glycans of interest from each sample based upon said mass spectrum.

2. The method according to claim 1 wherein said samples are cell samples.

3. The method according to claim 1 wherein said samples are cell samples and said first cell sample is modulated by exposing a precursor cell population to differentiation agents to differentiate said precursor cell to a differentiated cell.

4. The method according to claim 1 wherein said modulating step comprises exposing said first cell sample to a drug or hormone.

5. The method according to claim 1 wherein said modulating step comprises exposing said sample to one or more modified culture conditions to assess the impact of the modified culture conditions on the production of cells or tissue.

6. The method according to claim 1 wherein after said separation step, said proteins are digested into a plurality of peptides.

7. The method according to claim 1 wherein said proteins and/or lipids are further separated into proteins and/or lipids which are bound to glycans and proteins and/or lipids which are free from glycans.

8. The method according to claim 1 wherein said glycans are released and separated from said proteins and/or lipids.

9. The method according to claim 1 wherein said glycans are subjected to NMR analysis in addition to mass spectroscopy.

10. The method according to claim 1 further comprising the step of determining the structure of said glycans of interest from said mass spectrum.

11. The method according to claim 9 further comprising the step of determining the structure of said glycans of interest from said mass spectrum and said NMR analysis.

12. The method according to claim 5 wherein said peptides are further separated into peptides which contain glycans and peptides which do not contain glycans.

13. The method according to claim 12 wherein said peptides which contain glycans are subjected to mass spectroscopy and optionally, NMR analysis, to determine the peptide binding site of said glycans.

14. The method according to claim 1 wherein said separated lipids are further separated into lipids which contain glycans and lipids which do not contain glycans.

15. The method according to claim 14 wherein said lipids which contain glycans are subjected to mass spectroscopy and optionally, NMR analysis, to determine the binding site of said glycans.

16. The method according to claim 1 wherein said culture medium is a minimum essential medium which optionally comprises growth factors, retinoic acid, glucose, non-essential amino acids, salts (including trace elements), light or heavy glutamine, insulin, transferrin, beta mercaptoethanol and mixtures thereof.

17. The method according to claim 16 wherein said culture medium is Dulbecco's modified Eagle's medium (DMEM) supplemented with 10% fetal calf serum, 2 mM heavy L-glutamine or 2 mM light L-glutamine and 0.1 mM 2-mercaptoethanol.

18. The method according to claim 6 wherein said protein is digested with a proteolytic enzyme.

19. A method for comparing the relative abundance of one or more glycans of interest in a modulated biological sample compared to a control sample comprising:
    culturing a first biological sample to be modulated in a first culture medium further comprising $^{15}$N-glutamine;
    culturing a control sample in a second culture medium identical to said first culture medium further comprising $^{14}$N-glutamine;
    modulating said first sample during culturing;
    processing said first sample and said control sample to extract proteins and/or lipids therefrom;
    separating said proteins and/or lipids from said samples after said processing step;
    optionally digesting said proteins into a plurality of peptides;
    releasing glycans from said proteins, peptides and/or lipids and separating said release glycans from said proteins, peptides and/or lipids;
    subjecting said glycans to mass spectroscopy to develop a mass spectrum; and
    determining the relative abundance of said glycans of interest from each sample based upon said mass spectrum.

20. A method for comparing the relative abundance of one or more glycans of interest in a modulated biological sample compared to a control sample comprising:
    culturing a first biological sample to be modulated in a first culture medium further comprising $^{15}$N-glutamine;
    culturing a control sample in a second culture medium identical to said first culture medium further comprising $^{14}$N-glutamine;
    modulating said first sample during culturing;
    processing said first sample and said control sample to extract proteins and/or lipids therefrom;
    separating said proteins and/or lipids from said samples after said processing step;
    digesting said proteins into a plurality of peptides;
    releasing glycans from said proteins, peptides and/or lipids and separating said release glycans from said proteins, peptides and/or lipids;
    subjecting said glycans to mass spectroscopy to develop a mass spectrum; and
    determining the relative abundance of said glycans of interest from each sample based upon said mass spectrum.

* * * * *